(12) United States Patent
Jaeger et al.

(10) Patent No.: US 9,504,446 B2
(45) Date of Patent: Nov. 29, 2016

(54) SYSTEMS AND METHODS FOR COUPLING AN ULTRASOUND SOURCE TO TISSUE

(75) Inventors: Paul Jaeger, Mesa, AZ (US); Peter G. Barthe, Phoenix, AZ (US); Michael H. Slayton, Tempe, AZ (US)

(73) Assignee: GUIDED THERAPY SYSTEMS, LLC, Mesa, AZ (US)

( * ) Notice: Subject to any disclaimer, the term of this patent is extended or adjusted under 35 U.S.C. 154(b) by 600 days.

(21) Appl. No.: 13/547,023

(22) Filed: Jul. 11, 2012

(65) Prior Publication Data

US 2013/0012838 A1 Jan. 10, 2013

Related U.S. Application Data

(63) Continuation-in-part of application No. 13/136,544, filed on Aug. 2, 2011.

(60) Provisional application No. 61/506,609, filed on Jul. 11, 2011, provisional application No. 61/506,610,
(Continued)

(51) Int. Cl.
*A61B 8/00* (2006.01)
*A61N 7/02* (2006.01)
(Continued)

(52) U.S. Cl.
CPC .............. *A61B 8/429* (2013.01); *A61B 8/56* (2013.01); *A61N 7/02* (2013.01); *A61B 2018/00642* (2013.01); *A61B 2018/00898* (2013.01); *A61B 2090/378* (2016.02); *A61N 2007/006* (2013.01);
(Continued)

(58) Field of Classification Search
CPC ................. A61B 8/429; A61B 8/56; A61B 2018/00642; A61B 2018/00898; A61B 2090/378; A61N 7/02; A61N 2007/0034; A61N 2007/006; A61N 2007/0095; A61N 2007/0091; A61N 2007/027
USPC .................................. 600/437–480; 601/2–4
See application file for complete search history.

(56) References Cited

U.S. PATENT DOCUMENTS 2,427,348 A 9/1947 Bond et al.
3,913,386 A 10/1975 Saglio
(Continued)

FOREIGN PATENT DOCUMENTS

DE 4029175 3/1992
DE 10140064 3/2003
(Continued)

OTHER PUBLICATIONS

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.
(Continued)

*Primary Examiner* — Long V Le
*Assistant Examiner* — Angela M Hoffa
(74) *Attorney, Agent, or Firm* — Quarles & Brady, LLP

(57) ABSTRACT

This disclosure provides systems and methods for sensing coupling of an ultrasound source to a target and for providing a constant average output of power from an ultrasound source. The systems and methods can include a frequency sweep function. The systems and methods can also include receiving reflected energy from an acoustic window and determining a feedback using the reflected energy. The systems and methods can also include comparing the feedback with a threshold level and using the comparison to determine if the ultrasound source is coupled with a target.

14 Claims, 6 Drawing Sheets

Related U.S. Application Data filed on Jul. 11, 2011, provisional application No. 61/369,782, filed on Aug. 2, 2010, provisional application No. 61/369,793, filed on Aug. 2, 2010, provisional application No. 61/369,806, filed on Aug. 2, 2010, provisional application No. 61/370,095, filed on Aug. 2, 2010.

(51) Int. Cl.
  *A61B 18/00* (2006.01)
  *A61N 7/00* (2006.01)

(52) U.S. Cl.
  CPC .......... *A61N 2007/0034* (2013.01); *A61N 2007/0091* (2013.01); *A61N 2007/0095* (2013.01); *A61N 2007/027* (2013.01)

(56) References Cited

U.S. PATENT DOCUMENTS

| | | | |
|---|---|---|---|
| 3,965,455 A | 6/1976 | Hurwitz | |
| 3,992,925 A | 11/1976 | Perilhou | |
| 4,039,312 A | 8/1977 | Patru | |
| 4,059,098 A | 11/1977 | Murdock | |
| 4,101,795 A | 7/1978 | Fukumoto | |
| 4,166,967 A | 9/1979 | Benes et al. | |
| 4,211,948 A | 7/1980 | Brisken et al. | |
| 4,211,949 A | 7/1980 | Brisken et al. | |
| 4,213,344 A | 7/1980 | Rose | |
| 4,276,491 A | 6/1981 | Daniel | |
| 4,315,514 A | 2/1982 | Drewes et al. | |
| 4,325,381 A | 4/1982 | Glenn | |
| 4,343,301 A | 8/1982 | Indech | |
| 4,372,296 A | 2/1983 | Fahim | |
| 4,379,145 A | 4/1983 | Masuho et al. | |
| 4,381,007 A | 4/1983 | Doss | |
| 4,381,787 A | 5/1983 | Hottinger | |
| 4,397,314 A | 8/1983 | Vaguine | |
| 4,409,839 A | 10/1983 | Taenzer | |
| 4,431,008 A | 2/1984 | Wanner et al. | |
| 4,441,486 A | 4/1984 | Pounds | |
| 4,452,084 A | 6/1984 | Taenzer | |
| 4,484,569 A | 11/1984 | Driller | |
| 4,507,582 A | 3/1985 | Glenn | |
| 4,513,749 A | 4/1985 | Kino | |
| 4,513,750 A | 4/1985 | Heyman et al. | |
| 4,527,550 A | 7/1985 | Ruggera et al. | |
| 4,528,979 A | 7/1985 | Marchenko | |
| 4,534,221 A | 8/1985 | Fife et al. | |
| 4,566,459 A | 1/1986 | Umemura et al. | |
| 4,567,895 A | 2/1986 | Putzke | |
| 4,586,512 A | 5/1986 | Do-huu | |
| 4,601,296 A | 7/1986 | Yerushalmi | |
| 4,603,702 A * | 8/1986 | Hwang et al. | 600/437 |
| 4,620,546 A | 11/1986 | Aida et al. | |
| 4,637,256 A | 1/1987 | Sugiyama et al. | |
| 4,646,756 A | 3/1987 | Watmough | |
| 4,663,358 A | 5/1987 | Hyon | |
| 4,668,516 A | 5/1987 | Duraffourd | |
| 4,672,591 A | 6/1987 | Breimesser et al. | |
| 4,680,499 A | 7/1987 | Umemura et al. | |
| 4,697,588 A | 10/1987 | Reichenberger | |
| 4,708,127 A * | 11/1987 | Abdelghani | 601/2 |
| 4,754,760 A | 7/1988 | Fukukita et al. | |
| 4,757,820 A | 7/1988 | Itoh | |
| 4,771,205 A | 9/1988 | Mequio | |
| 4,801,459 A | 1/1989 | Liburdy | |
| 4,803,625 A | 2/1989 | Fu et al. | |
| 4,807,633 A | 2/1989 | Fry | |
| 4,817,615 A | 4/1989 | Fukukita et al. | |
| 4,858,613 A | 8/1989 | Fry | |
| 4,860,732 A | 8/1989 | Hasegawa et al. | |
| 4,865,041 A | 9/1989 | Hassler | |
| 4,865,042 A | 9/1989 | Umemura | |
| 4,867,169 A | 9/1989 | Machida | |
| 4,874,562 A | 10/1989 | Hyon | |
| 4,875,487 A | 10/1989 | Seppi | |
| 4,891,043 A | 1/1990 | Zeimer et al. | |
| 4,893,624 A | 1/1990 | Lele | |
| 4,896,673 A | 1/1990 | Rose | |
| 4,900,540 A | 2/1990 | Ryan et al. | |
| 4,901,729 A | 2/1990 | Saitoh et al. | |
| 4,917,096 A | 4/1990 | Englehart | |
| 4,932,414 A | 6/1990 | Coleman et al. | |
| 4,938,216 A | 7/1990 | Lele | |
| 4,938,217 A | 7/1990 | Lele | |
| 4,947,046 A | 8/1990 | Kawabata et al. | |
| 4,951,653 A | 8/1990 | Fry | |
| 4,955,365 A | 9/1990 | Fry | |
| 4,958,626 A | 9/1990 | Nambu | |
| 4,976,709 A | 12/1990 | Sand | |
| 4,979,501 A | 12/1990 | Valchanov | |
| 4,992,989 A | 2/1991 | Watanabe et al. | |
| 5,012,797 A | 5/1991 | Liang | |
| 5,018,508 A | 5/1991 | Fry et al. | |
| 5,030,874 A | 7/1991 | Saito et al. | |
| 5,036,855 A | 8/1991 | Fry | |
| 5,040,537 A | 8/1991 | Katakura | |
| 5,054,310 A | 10/1991 | Flynn | |
| 5,054,470 A | 10/1991 | Fry | |
| 5,070,879 A | 12/1991 | Herres | |
| 5,088,495 A | 2/1992 | Miyagawa | |
| 5,115,814 A | 5/1992 | Griffith | |
| 5,117,832 A | 6/1992 | Sanghvi | |
| 5,123,418 A | 6/1992 | Saurel | |
| 5,143,063 A | 9/1992 | Fellner | |
| 5,143,074 A | 9/1992 | Dory | |
| 5,149,319 A | 9/1992 | Unger | |
| 5,150,711 A | 9/1992 | Dory | |
| 5,150,714 A | 9/1992 | Green | |
| 5,152,294 A | 10/1992 | Mochizuki et al. | |
| 5,156,144 A | 10/1992 | Iwasaki et al. | |
| 5,158,536 A | 10/1992 | Sekins | |
| 5,159,931 A | 11/1992 | Pini | |
| 5,163,421 A | 11/1992 | Bernstein et al. | |
| 5,163,436 A | 11/1992 | Saitoh et al. | |
| 5,178,135 A | 1/1993 | Uchiyama et al. | |
| 5,190,518 A | 3/1993 | Takasu | |
| 5,190,766 A | 3/1993 | Ishihara | |
| 5,191,880 A | 3/1993 | McLeod | |
| 5,205,287 A | 4/1993 | Erbel et al. | |
| 5,209,720 A | 5/1993 | Unger | |
| 5,212,671 A | 5/1993 | Fujii et al. | |
| 5,215,680 A | 6/1993 | D'Arrigo | |
| 5,224,467 A | 7/1993 | Oku | |
| 5,230,334 A | 7/1993 | Klopotek | |
| 5,230,338 A | 7/1993 | Allen et al. | |
| 5,247,924 A | 9/1993 | Suzuki et al. | |
| 5,255,681 A | 10/1993 | Ishimura et al. | |
| 5,257,970 A | 11/1993 | Dougherty | |
| 5,265,614 A | 11/1993 | Hayakawa | |
| 5,267,985 A | 12/1993 | Shimada et al. | |
| 5,269,297 A | 12/1993 | Weng | |
| 5,282,797 A | 2/1994 | Chess | |
| 5,295,484 A | 3/1994 | Marcus | |
| 5,295,486 A | 3/1994 | Wollschlager et al. | |
| 5,304,169 A | 4/1994 | Sand | |
| 5,305,756 A | 4/1994 | Entrekin et al. | |
| 5,321,520 A | 6/1994 | Inga et al. | |
| 5,323,779 A | 6/1994 | Hardy et al. | |
| 5,327,895 A | 7/1994 | Hashimoto et al. | |
| 5,348,016 A | 9/1994 | Unger et al. | |
| 5,360,268 A | 11/1994 | Hayashi | |
| 5,370,121 A | 12/1994 | Reichenberger | |
| 5,371,483 A | 12/1994 | Bhardwaj | |
| 5,375,602 A | 12/1994 | Lancee et al. | |
| 5,379,773 A | 1/1995 | Hornsby | |
| 5,380,280 A | 1/1995 | Peterson | |
| 5,380,519 A | 1/1995 | Schneider et al. | |
| 5,383,917 A | 1/1995 | Desai et al. | |
| 5,391,140 A | 2/1995 | Schaetzle | |
| 5,391,197 A | 2/1995 | Burdette et al. | |
| 5,392,259 A | 2/1995 | Bolorforosh | |
| 5,396,143 A | 3/1995 | Seyed-Bolorforosh et al. | |

(56) References Cited

U.S. PATENT DOCUMENTS

| | | |
|---|---|---|
| 5,398,689 A | 3/1995 | Connor et al. |
| 5,406,503 A | 4/1995 | Williams, Jr. et al. |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura |
| 5,438,998 A | 8/1995 | Hanafy |
| 5,458,596 A | 10/1995 | Lax |
| 5,460,179 A | 10/1995 | Okunuki et al. |
| 5,460,595 A | 10/1995 | Hall et al. |
| 5,469,854 A | 11/1995 | Unger et al. |
| 5,471,988 A | 12/1995 | Fujio |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,654,509 A * | 8/1997 | Miele et al. .................. 73/602 |
| 5,655,535 A | 8/1997 | Friemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,687,737 A | 11/1997 | Branham et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi |
| 5,876,431 A | 3/1999 | Spehr et al. |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder et al. |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fullmer |
| 5,971,949 A | 10/1999 | Levin |
| 5,977,538 A | 11/1999 | Unger et al. |
| 5,984,882 A | 11/1999 | Rosenschein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,016,255 A | 1/2000 | Bolan et al. |
| 6,019,724 A | 2/2000 | Gronningsaeter et al. |
| 6,022,308 A | 2/2000 | Williams |
| 6,022,327 A | 2/2000 | Chang |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach et al. |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |

(56) References Cited

U.S. PATENT DOCUMENTS

| | | |
|---|---|---|
| 6,113,558 A | 9/2000 | Rosenschein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Digs et al. |
| 6,190,336 B1 | 2/2001 | Duarte |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,273,884 B1 * | 8/2001 | Altshuler et al. ............... 606/9 |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas et al. |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi et al. |
| 6,491,657 B2 | 12/2002 | Rowe |
| 6,500,121 B1 | 12/2002 | Slayton |
| 6,500,141 B1 | 12/2002 | Irion |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk et al. |
| 6,524,250 B1 | 2/2003 | Weber |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,607,498 B2 | 8/2003 | Eshel |
| 6,610,011 B2 * | 8/2003 | Emery ..................... 600/437 |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin |
| 6,669,638 B1 | 12/2003 | Miller et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |

(56) References Cited

U.S. PATENT DOCUMENTS

| | | | |
|---|---|---|---|
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco et al. |
| 7,303,555 B2 | 12/2007 | Makin et al. |
| 7,327,071 B2 | 2/2008 | Nishiyama et al. |
| 7,331,951 B2 | 2/2008 | Eshel et al. |
| 7,332,985 B2 | 2/2008 | Larson, III et al. |
| 7,338,446 B2 * | 3/2008 | MacDonald et al. ......... 600/437 |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,510,536 B2 | 3/2009 | Foley et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,686,763 B2 | 3/2010 | Vaezy et al. |
| 7,695,437 B2 | 4/2010 | Quistgaard et al. |
| 7,758,524 B2 | 7/2010 | Barthe |
| 7,789,841 B2 | 9/2010 | Huckle et al. |
| 7,824,348 B2 | 11/2010 | Barthe et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,281 B2 | 6/2011 | Pedersen et al. |
| 7,967,764 B2 | 6/2011 | Lidgren et al. |
| 7,967,839 B2 | 6/2011 | Flock et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,831,710 B2 * | 9/2014 | Kobayashi ................. 600/478 |
| 2001/0009997 A1 | 7/2001 | Pope |
| 2001/0009999 A1 | 7/2001 | Kaufman et al. |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0052550 A1 | 5/2002 | Madsen et al. |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0072691 A1 | 6/2002 | Thompson et al. |
| 2002/0082501 A1 | 6/2002 | Emery |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton et al. |
| 2002/0095143 A1 | 7/2002 | Key |
| 2002/0099094 A1 | 7/2002 | Anderson |
| 2002/0115917 A1 | 8/2002 | Honda et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | Mchale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |

(56) References Cited

U.S. PATENT DOCUMENTS

| | | |
|---|---|---|
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom et al. |
| 2004/0041563 A1 | 3/2004 | Lewin et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Simske |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste et al. |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1 | 3/2005 | Maki et al. |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 | 5/2005 | Larson, III et al. |
| 2005/0113689 A1 | 5/2005 | Gritzky |
| 2005/0134314 A1 | 6/2005 | Prather et al. |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard et al. |
| 2005/0197681 A1 | 9/2005 | Barolet et al. |
| 2005/0228281 A1 | 10/2005 | Nefos |
| 2005/0240170 A1 | 10/2005 | Zhang et al. |
| 2005/0251120 A1 | 11/2005 | Anderson et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0261584 A1 | 11/2006 | Blackburn |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0060819 A1* | 3/2007 | Altshuler et al. ............. 600/475 |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0027328 A1 | 1/2008 | Klopotek et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pedersen |
| 2008/0139974 A1 | 6/2008 | Da Silva |
| 2008/0146970 A1 | 6/2008 | Litman et al. |
| 2008/0167556 A1* | 7/2008 | Thompson et al. .......... 600/439 |
| 2008/0183077 A1 | 7/2008 | Moreau-Gobard et al. |
| 2008/0188745 A1 | 8/2008 | Chen et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1* | 11/2008 | Slayton et al. .................. 601/2 |
| 2008/0281255 A1 | 11/2008 | Slayton |
| 2008/0294073 A1 | 11/2008 | Barthe |
| 2008/0319356 A1 | 12/2008 | Cain et al. |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0069677 A1 | 3/2009 | Chen et al. |
| 2009/0093737 A1 | 4/2009 | Chomas et al. |
| 2009/0156969 A1 | 6/2009 | Santangelo |

(56) References Cited

U.S. PATENT DOCUMENTS

| | | |
|---|---|---|
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0299175 A1 | 12/2009 | Bernstein et al. |
| 2009/0318909 A1 | 12/2009 | Debenedictis et al. |
| 2010/0011236 A1 | 1/2010 | Barthe et al. |
| 2010/0022919 A1 | 1/2010 | Peterson |
| 2010/0022922 A1 | 1/2010 | Barthe et al. |
| 2010/0042020 A1 | 2/2010 | Ben-Ezra |
| 2010/0049178 A1 | 2/2010 | Deem et al. |
| 2010/0063422 A1 | 3/2010 | Hynynen et al. |
| 2010/0066207 A1 | 3/2010 | Saito |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241034 A1 | 9/2010 | Little |
| 2010/0241035 A1 | 9/2010 | Barthe et al. |
| 2010/0280420 A1 | 11/2010 | Barthe et al. |
| 2010/0286518 A1 | 11/2010 | Lee et al. |
| 2011/0040171 A1 | 2/2011 | Foley et al. |
| 2011/0040190 A1 | 2/2011 | Jahnke et al. |
| 2011/0087099 A1 | 4/2011 | Eshel et al. |
| 2011/0087255 A1 | 4/2011 | Mccormack et al. |
| 2011/0112405 A1 | 5/2011 | Barthe et al. |
| 2011/0178444 A1 | 7/2011 | Slayton et al. |
| 2011/0190745 A1 | 8/2011 | Uebelhoer et al. |
| 2011/0264012 A1 | 10/2011 | Lautzenhiser et al. |
| 2012/0004549 A1 | 1/2012 | Barthe et al. |
| 2012/0016239 A1 | 1/2012 | Barthe et al. |
| 2012/0029353 A1* | 2/2012 | Slayton et al. ............... 600/439 |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |
| 2012/0271294 A1 | 10/2012 | Barthe et al. |
| 2012/0296240 A1 | 11/2012 | Azhari et al. |
| 2012/0316426 A1 | 12/2012 | Foley et al. |
| 2012/0323095 A1* | 12/2012 | Baker, Jr. ............... 600/324 |
| 2012/0330194 A1* | 12/2012 | Britva et al. ............... 601/2 |
| 2012/0330197 A1 | 12/2012 | Makin et al. |
| 2012/0330222 A1 | 12/2012 | Barthe et al. |
| 2012/0330223 A1 | 12/2012 | Makin et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018286 A1 | 1/2013 | Slayton et al. |
| 2013/0046209 A1 | 2/2013 | Slayton et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0172757 A1* | 7/2013 | Frigstad et al. ............... 600/459 |
| 2013/0190659 A1 | 7/2013 | Slayton et al. |
| 2013/0211258 A1 | 8/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310863 A1 | 11/2013 | Barthe et al. |
| 2014/0058264 A1* | 2/2014 | Baym et al. ............... 600/447 |
| 2014/0082907 A1 | 3/2014 | Barthe |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0319623 A1 | 6/1989 |
| EP | 0344773 | 12/1989 |
| EP | 1479412 | 11/1991 |
| EP | 0473553 | 4/1992 |
| EP | 0661029 | 7/1995 |
| EP | 1050322 | 11/2000 |
| EP | 1234566 | 8/2002 |
| EP | 1262160 | 12/2002 |
| EP | 1374944 A | 1/2004 |
| GB | 2113099 | 8/1983 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 11506636 | 6/1999 |
| JP | 2000166940 | 6/2000 |
| JP | 2001170068 | 6/2001 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2007505793 A | 3/2007 |
| JP | 2009518126 | 5/2009 |
| JP | 2010517695 | 5/2010 |
| KR | 1020010024871 | 3/2001 |
| KR | 100400870 B1 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | 9625888 | 8/1996 |
| WO | 9639079 A1 | 12/1996 |
| WO | 9735518 | 10/1997 |
| WO | 9832379 | 7/1998 |
| WO | 9933520 | 7/1999 |
| WO | 9949788 | 10/1999 |
| WO | 0006032 | 2/2000 |
| WO | 0015300 | 3/2000 |
| WO | 0021612 | 4/2000 |
| WO | 0053113 | 9/2000 |
| WO | 0128623 | 4/2001 |
| WO | 0182777 | 11/2001 |
| WO | 0182778 | 11/2001 |
| WO | 0187161 | 11/2001 |
| WO | 0209813 | 2/2002 |
| WO | 02024050 | 3/2002 |
| WO | 02092168 A | 11/2002 |
| WO | 020292168 | 11/2002 |

(56) References Cited

FOREIGN PATENT DOCUMENTS

| WO | 03053266 A | 7/2003 |
|---|---|---|
| WO | 03065347 | 8/2003 |
| WO | 03070105 | 8/2003 |
| WO | 03077833 | 8/2003 |
| WO | 03086215 | 10/2003 |
| WO | 03096883 | 11/2003 |
| WO | 03099177 | 12/2003 |
| WO | 03101530 | 12/2003 |
| WO | 2004000116 A | 12/2003 |
| WO | 2004080147 | 9/2004 |
| WO | 2004110558 | 12/2004 |
| WO | 2005004972 A1 | 1/2005 |
| WO | 2005011804 A | 2/2005 |
| WO | 2005065408 | 7/2005 |
| WO | 2005090978 | 9/2005 |
| WO | 2006036870 | 4/2006 |
| WO | 2006042163 A | 4/2006 |
| WO | 2006042168 | 4/2006 |
| WO | 2006042201 | 4/2006 |
| WO | 2006065671 | 6/2006 |
| WO | 2006082573 | 8/2006 |
| WO | 2007067563 A | 6/2007 |
| WO | 2008024923 A2 | 2/2008 |
| WO | 2008036622 A | 3/2008 |
| WO | 2009013729 | 1/2009 |
| WO | 2009149390 A1 | 12/2009 |
| WO | 2014055708 A1 | 4/2014 |

OTHER PUBLICATIONS

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jenne, J., et al., "Temperature Mapping for High Energy US—Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Mitragotri, Samir; "Healing sound: the use of ultrasound in drug delivery and other therapeutic applications," Nature Reviews; Drug Delivery, pp. 255-260, vol. 4.

Sanghvi, N.T., et al., "Transrectal Ablation of Prostate Tissue Using Focused Ultrasound," 1993 Ultrasonics Symposium, IEEE, pp. 1207-1210.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Smith, Nadine Barrie, et al., "Non-Invasive in Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Sassen, Sander, "ATI's R520 architecture, the new king of the hill?" http://www.hardwareanalysis.com/content/article/1813, Sep. 16, 2005, 2 pages.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

European Examination Report in related Application No. 05808908.7 dated Jun. 29, 2009.

European Examination Report in related Application No. 05810308.6 dated Jun. 29, 2009.

European Examination Report in related Application No. 10185100.4 dated Jan. 6, 2014.

European Examination Report in related Application No. 10185120.2 dated Jan. 22, 2014.

Decision of the Korean Intellectual Property Tribunal dated Jun. 28, 2013 regarding Korean Patent No. 10-1142108, which is related to the pending application and/or an application identified in the Table on pp. 2-5 of the information Disclosure Statement herein (English translation, English translation certifications, and Korean decision included).

(56) References Cited

OTHER PUBLICATIONS

International Search Report and Written Opinion dated Jan. 23, 2014 in Application No. PCT/US2012/046122.
International Search Report and Written Opinion dated Jan. 23, 2014 in Application No. PCT/US2012/046123.
International Search Report and Written Opinion dated Jan. 28, 2012 in Application No. PCT/US2012/046327.
International Search Report and Written Opinion dated Jan. 28, 2013 in Application No. PCT/US2012/046125.
International Search Report and Written Opinion dated Feb. 14, 2013 in Application No. PCT/US2011/001361.
International Search Report and Written Opinion dated Feb. 14, 2013 in Application No. PCT/US2011/001362.
International Search Report and Written Opinion dated Feb. 14, 2013 in Application No. PCT/US2011/001366.
International Search Report and Written Opinion dated Apr. 6, 2012 in Application No. PCT/US2011/001367.
Calderhead et al, One Mechanism Behind LED Photo-Therapy for Wound Healing and Skin Rejuvenation: Key Role of the Mast Cell, Laser Therapy, Jul. 2008, pp. 141-148, 17.3.
European Examination Report in related Application No. 09835856.7 dated Apr. 11, 2004.
International Search Report and Written Opinion dated Apr. 6, 2012 in Application No. PCT/US2011/001366.
International Search Report and Written Opinion dated Apr. 12, 2012 in Application No. PCT/US2011/001361.
Arthur et al., "Non-invasive estimation of hyperthermia temperatures with ultrasound," Int. J. Hyperthermia, Sep. 2005, 21(6), pp. 589-600.
Chen, L. et al., ""Effect of Blood Perfusion on the ablation of liver perenchyma with high intensity focused ultrasound,"" Phys. Med. Biol; 38:1661-1673; 1993b.
Damianou et al., Application of the Thermal Dose Concept for Predicting the Necrosed Tissue Volume During Ultrasound Surgery, 1993 IEEE Ultrasound Symposium, pp. 1199-1202.
Fry, W.J. et al., "Production of Focal Destructive Lesions in the Central Nervous System with Ultrasound," J. Neurosurg., 11:471-478; 1954.
Harr, G.R. et al., "Tissue Destruction with Focused Ultrasound in Vivo," Eur. Urol. 23 (suppl. 1):8-11; 1993.
Jeffers et al., "Evaluation of the Effect of Cavitation Activity on Drug-Ultrasound Synergisms," 1993 IEEE Ultrasonics Symposium, pp. 925-928.
Madersbacher, S. et al., "Tissue Ablation in Bening Prostatic Hyperplasia with High Intensity Focused Ultrasound," Dur. Urol., 23 (suppl. 1):39-43; 1993.
Saad et al., "Ultrasound-Enhanced Effects of Adriamycin Against Murine Tumors," Ultrasound in Med. & Biol. vol. 18, No. 8, pp. 715-723 (1992).
Simon et al., "Applications of Lipid-Coated Microbubble Ultrasonic Contrast to Tumor Therapy," Ultrasound in Med. & Biol. vol. 19, No. 2, pp. 123-125 (1993).
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
PCT International Search Report and Written Opinion, PCT/US2014/030779, Sep. 1, 2014, 8 pages.
European Patent Office, Examination Report, EP 07814933.3, Aug. 5, 2014, 5 pages.
European Patent Office, Examination Report, EP 05798870.1, Oct. 20, 2014, 5 pages.
European Patent Office, Examination Report, EP 10185100.4, Oct. 24, 2014, 4 pages.
European Patent Office, Examination Report, EP 10185112.9, Oct. 24, 2014, 5 pages.
European Patent Office, Examination Report, EP 10185117.8, Oct. 24, 2014, 5 pages.
European Patent Office, Examination Report, EP 10185120.2, Oct. 24, 2014, 4 pages.
Kelly, et al., An Air-Coupled Ultrasonic Matching Layer Employing Half Wavelength Cavity Resonance, 2001 IEEE Ultrasonics Symposium, vol. 2, pp. 965-968.
European Patent Office, Supplementary Partial European Search Report, Application No. 12814300.5, Mar. 20, 2015, 8 pages.

* cited by examiner

# SYSTEMS AND METHODS FOR COUPLING AN ULTRASOUND SOURCE TO TISSUE

CROSS-REFERENCE TO RELATED APPLICATIONS

This application claims priority to and the benefit of U.S. Provisional Patent Application Ser. No. 61/506,609, entitled "Systems and Methods for Monitoring Ultrasound Power Efficiency," filed Jul. 11, 2011; and U.S. Provisional Patent Application Ser. No. 61/506,610, entitled "Methods and Systems for Controlling Acoustic Energy Deposition into a Medium," filed Jul. 11, 2011; all of which are incorporated by reference herein.

This application is a continuation in part of and claims priority to and the benefit of U.S. patent application Ser. No. 13/136,544, entitled "Systems and Methods for Ultrasound Treatment," filed Aug. 2, 2011, which claims priority to and the benefit of U.S. Provisional Patent Application Ser. No. 61/369,782, entitled "Systems and Methods for Ultrasound Treatment", filed Aug. 2, 2010; U.S. Provisional Patent Application Ser. No. 61/369,793, entitled "System and Method for Treating Sports Related Injuries", filed Aug. 2, 2010; U.S. Provisional Patent Application Ser. No. 61/369,806, entitled "System and Method for Treating Sports Related Injuries", filed Aug. 2, 2010; U.S. Provisional Patent Application Ser. No. 61/370,095, entitled "System and Method for Treating Cartilage", filed Aug. 2, 2010; all of which are incorporated by reference herein.

BACKGROUND

Coupling of a treatment system to tissue is important for clinical efficiency of the desired treatment. In addition, using a treatment system that is not coupled to tissue may cause safety concerns. Further, if a treatment system is not properly coupled to the tissue may cause stability and performance issues. Various contact sensors have been used to determine if a treatment system is coupled to targeted tissue. However, these contact sensors typically use mechanical methods to determine if a treatment system is coupled to the tissue. Accordingly, new approaches for determining whether a treatment system is coupled to targeted tissue are needed.

SUMMARY

Various embodiments described herein provide methods and systems for monitoring ultrasound energy. Various embodiments provide a method of sensing coupling of an ultrasound source to a target. In some embodiments, the method comprises providing an ultrasound sound source comprising a transducer, an acoustically transparent standoff, an acoustic window at a bottom surface of the standoff, and a frequency sweep function coupled to the transducer. In some embodiments, the method can comprise emitting ultrasound energy from the transducer; receiving reflected energy; frequency sweeping the transducer; determining the feedback from the frequency sweep is above a threshold level; and determining of the source is coupled to the target.

In some embodiments, if the feedback from the frequency is above the threshold level, then the source is not coupled to the target. In some embodiments, if the feedback from the frequency is below the threshold level, then the source is coupled to the target.

Various embodiments provide a system for determining whether an ultrasound source is coupled to a target. In some embodiments, the system comprises an ultrasound source comprising a transducer; an acoustically transparent standoff coupled to the transducer; a half wavelength acoustic window at a bottom surface of the standoff, and a frequency sweep function coupled to the transducer.

Various embodiments provide a system for providing a constant average output of power from an ultrasound source. In some embodiments, the system comprises an ultrasound transducer coupled to a power supply; a controller in communication with the power supply; a chirp function in communication with and operable to monitor the ultrasound transducer; a feedback loop from the chirp function to the controller. In some embodiments, the controller is operable to change a parameter on the transducer based on the feedback to provide a constant average output of power from the ultrasound transducer.

DRAWINGS

The present disclosure will become more fully understood from the description and the accompanying drawings, wherein.

DESCRIPTION

Figure 1:
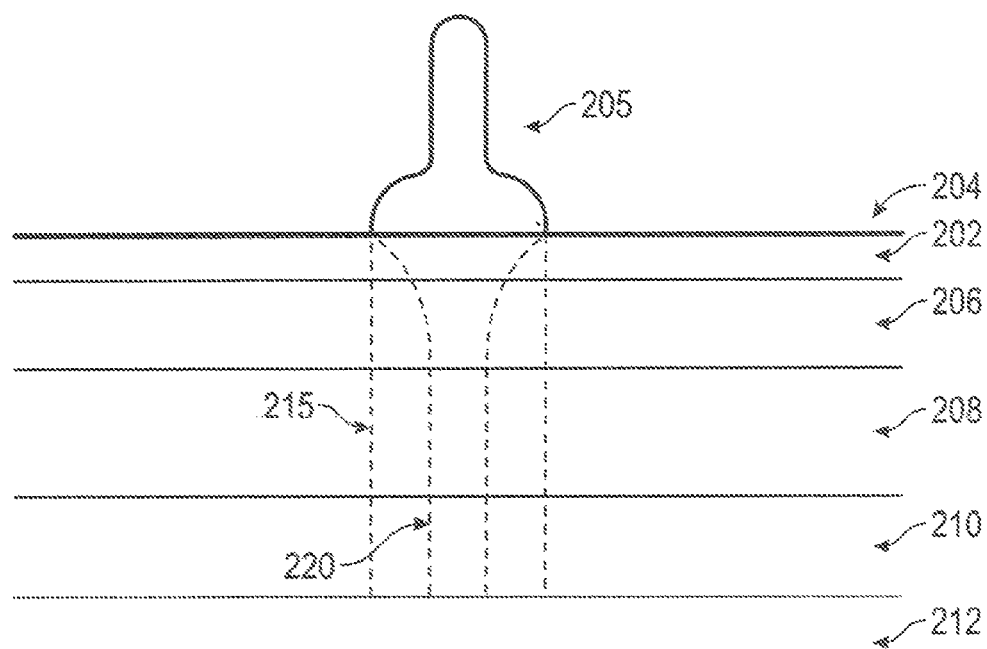
FIG. 1 is a cross sectional view illustrating tissue layers and ultrasound energy directed to a portion of the tissue layers, in accordance with various non-limiting embodiments.

The following description is merely exemplary in nature and is in no way intended to limit the various embodiments, their application, or uses. As used herein, the phrase "at least one of A, B, and C" should be construed to mean a logical (A or B or C), using a non-exclusive logical "or." As used herein, the phrase "A, B and/or C" should be construed to mean (A, B, and C) or alternatively (A or B or C), using a non-exclusive logical "or." It should be understood that steps within a method may be executed in different order without altering the principles of the present disclosure.

The drawings described herein are for illustrative purposes only of selected non-limiting embodiments and not all possible implementations, and are not intended to limit the scope of any of the various embodiments disclosed herein or any equivalents thereof. It is understood that the drawings are not drawn to scale. For purposes of clarity, the same reference numbers will be used in the drawings to identify similar elements.

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices. In addition, the embodiments may be practiced in any number of medical contexts and that the various embodiments relating to a method and system for acoustic energy deposition in tissue, as described herein, are merely indicative of one of the many applications for the invention. For example, the principles, features and methods discussed may be applied to any medical application. Further, various aspects of the various embodiments may be suitably applied to cosmetic applications. Moreover, some of the embodiments may be applied to cosmetic enhancement of skin and/or various soft tissue layers.

Various embodiments provide methods and systems to adjust a temperature of a transducer, in order to maintain maximum efficiency of power applied by the transducer. Some embodiments provide methods and systems to minimize or eliminate temperature saturation of a transducer during the delivery of power to the transducer. In some embodiments, methods and systems can control a temperature of a transducer to maintain a desired frequency of energy transmission at a maximum power.

Various embodiments provide methods and systems to adjust a temperature of a transducer, in order to maintain maximum efficiency of power applied by the transducer. Some embodiments provide methods and systems to minimize or eliminate temperature saturation of a transducer during the delivery of power to the transducer. In some embodiments, methods and systems can control a temperature of a transducer to maintain a desired frequency of energy transmission at a maximum power.

Some embodiments provide a method of providing ultrasound energy having a stable power output. The method can comprise providing ultrasound energy from a ultrasound transducer; determining a power level threshold of the ultrasound energy; monitoring a power level of the ultrasound energy over time of the ultrasound energy; communicating a power level to a controller; adjusting the frequency of the ultrasound energy upon a change in the power level; and maintaining the power level threshold of the ultrasound energy.

In some embodiments, the method can further comprise emitting the ultrasound energy at a specific frequency and correcting the frequency to the specific frequency upon a change in the power level. In some embodiments, the method can comprise changing power provided to a transducer providing the ultrasound energy based on the adjusting the frequency of the ultrasound energy. In some embodiments, the method can comprise terminating the providing the ultrasound energy upon a change of the power level above the power level threshold.

Some embodiments provide a method of providing ultrasound energy having a stable power output. The method can comprise providing ultrasound energy from an ultrasound transducer; determining a power level threshold of the ultrasound energy; monitoring a temperature of the ultrasound transducer over time; communicating the temperature to a controller; adjusting the frequency of the ultrasound energy upon a change in the temperature; and maintaining the power level threshold of the ultrasound energy.

In some embodiments, the method can further comprise determining a temperature threshold of the ultrasound transducer and terminating the providing ultrasound energy when the temperature is above the temperature threshold.

In some embodiments, the method can further comprise emitting the ultrasound energy at a specific frequency and correcting the frequency to the specific frequency upon the change of temperature. In some embodiments, the method can comprise terminating the providing the ultrasound energy upon a change of the power level above the power level threshold. In some embodiments, the method can further comprise determining a temperature threshold of the ultrasound transducer and terminating the providing ultrasound energy when a temperature of the ultrasound transducer is above the temperature threshold.

Some embodiments provide a method of providing ultrasound energy having a stable power output. The method can comprise providing ultrasound energy from an ultrasound transducer; determining a voltage threshold of the ultrasound energy; monitoring a voltage of the ultrasound transducer over time; communicating the voltage to a controller; adjusting the frequency of the ultrasound energy upon a change in the voltage; and maintaining the power level threshold of the ultrasound energy.

In some embodiments, the method can further comprise determining a temperature threshold of the ultrasound transducer and terminating the providing ultrasound energy when the temperature of the ultrasound transducer is above the temperature threshold.

In some embodiments, the method can further comprise emitting the ultrasound energy at a specific frequency and correcting the frequency to the specific frequency upon the change of voltage. In some embodiments, the method can comprise terminating the providing the ultrasound energy upon a change of the power level above the power level threshold.

Some embodiments provide a method of providing ultrasound energy having a stable power output. The method can comprise providing ultrasound energy from a ultrasound transducer; determining a voltage threshold of the ultrasound energy; monitoring a voltage of the ultrasound transducer over time; communicating the voltage to a controller; adjusting the frequency of the ultrasound energy upon an change in the voltage; monitoring a power level of the ultrasound energy over time of the ultrasound energy; communicating a power level to a controller; adjusting the frequency of the ultrasound energy upon a change in the power level; and maintaining the power level threshold of the ultrasound energy.

In some embodiments, the method can further comprise determining a temperature threshold of the ultrasound transducer and terminating the providing ultrasound energy when the temperature of the ultrasound transducer is above the temperature threshold.

In some embodiments, the method can further comprise emitting the ultrasound energy at a specific frequency and correcting the frequency to the specific frequency upon the change of voltage. In some embodiments, the method can comprise terminating the providing the ultrasound energy upon a change of the power level above the power level threshold.

Some embodiments provide a method of providing ultrasound energy having a stable power output. The method can comprise providing ultrasound energy from a ultrasound transducer; monitoring a power level of the ultrasound energy over time of the ultrasound energy; communicating a power level to a controller; adjusting the frequency of the ultrasound energy upon a change in the power level; monitoring a temperature of the ultrasound transducer over time; communicating the temperature to a controller; adjusting the frequency of the ultrasound energy upon an change in the temperature; and maintaining the power level threshold of the ultrasound energy.

In some embodiments, the method can further comprise determining a temperature threshold of the ultrasound transducer and terminating the providing ultrasound energy when the temperature of the ultrasound transducer is above the temperature threshold.

In some embodiments, the method can further comprise emitting the ultrasound energy at a specific frequency and correcting the frequency to the specific frequency upon the change of voltage. In some embodiments, the method can comprise terminating the providing the ultrasound energy upon a change of the power level above the power level threshold.

Some embodiments provide a method of providing ultrasound energy having a stable power output. The method can comprise providing ultrasound energy from a ultrasound transducer; determining a voltage threshold of the ultrasound energy; monitoring a voltage of the ultrasound transducer over time; communicating the voltage to a controller; adjusting the frequency of the ultrasound energy upon an change in the voltage; monitoring a power level of the ultrasound energy over time of the ultrasound energy; communicating a power level to a controller; adjusting the frequency of the ultrasound energy upon a change in the power level; monitoring a temperature of the ultrasound transducer over time; communicating the temperature to a controller; adjusting the frequency of the ultrasound energy upon an change in the temperature; and maintaining the power level threshold of the ultrasound energy.

In some embodiments, the method can further comprise determining a temperature threshold of the ultrasound transducer and terminating the providing ultrasound energy when the temperature of the ultrasound transducer is above the temperature threshold.

In some embodiments, the method can further comprise emitting the ultrasound energy at a specific frequency and correcting the frequency to the specific frequency upon the change of voltage. In some embodiments, the method can comprise terminating the providing the ultrasound energy upon a change of the power level above the power level threshold.

In some embodiments, temperature can be monitored by monitoring changes in time of flight of the ultrasound energy from the transducer. In some embodiments, temperature can be monitored by a piezoelectric sensor that may be a portion of transducer, as described herein. In various embodiments, a controller may use a look up table to change a parameter. In some embodiments, controller can employ hardware, software, or a combination of both to change a parameter such as power, voltage or current.

With reference to FIG. 1, a cross sectional view of tissue layers and ultrasound energy directed to at least one of the tissue layers, according to various embodiments of the present invention, is illustrated. The tissue layers illustrated are skin surface 204, epidermal layer 202, dermis layer 206, fat layer 208, SMAS layer 210, and muscle and connective tissue layer 212. Ultrasound probe 205 transmits ultrasound energy 220 transmitting in ROI 215. In various embodiments, ultrasound probe 205 is capable of transmitting ultrasound energy 220 transmitting at variable depths in ROI 215, such as, for example, the depths described herein. Ultrasound probe 205 is capable of transmitting therapeutic ultrasound energy as a single frequency, variable frequencies, or a plurality of frequencies, such as, for example, within the frequency ranges described herein. Ultrasound probe 205 is capable of transmitting ultrasound energy 220 transmitting for variable time periods or to pulse the transmission over time, such as, for example, those time intervals described herein. Ultrasound probe 205 is capable of providing various energy levels of therapeutic ultrasound energy, such as, for example, the energy levels described herein.

Ultrasound probe 205 may be individual hand-held device, or may be part of a treatment system or part of cosmetic enhancement system. The ultrasound probe 205 can provide both therapeutic ultrasound energy and imaging ultrasound energy. However, ultrasound probe 205 may provide only therapeutic ultrasound energy. Ultrasound probe 205 may comprise a therapeutic transducer and a separate imaging transducer. Ultrasound probe 205 may comprise a transducer or a transducer array capable of both therapeutic and imaging applications. According an alternative embodiment, ultrasound probe 205 is coupled directly to one of the tissue layers, as opposed to skin surface 204 to treat the tissue layer. For example, ultrasound probe 205 can be integrated to or attached to a tool, such as, for example, an arthroscopic tool, laparoscopic tool, or an endoscopic tool that may be inserted into a patient's body with minimal invasiveness.

In various embodiments, the ultrasound energy level is in a range of about 0.1 joules to about 500 joules in order to create an ablative lesion. However, the ultrasound energy 108 level can be in a range of from about 0.1 joules to about 100 joules, or from about 1 joules to about 50 joules, or from about 0.1 joules to about 10 joules, or from about 50 joules to about 100 joules, or from about 100 joules to about 500 joules, or from about 50 joules to about 250 joules.

Further, the amount of time ultrasound energy is applied at these levels varies in the range from approximately 1 millisecond to several minutes. However, a range can be from about 1 millisecond to about 5 minutes, or from about 1 millisecond to about 1 minute, or from about 1 millisecond to about 30 seconds, or from about 1 millisecond to about 10 seconds, or from about 1 millisecond to about 1 second, or from about 1 millisecond to about 0.1 seconds, or about 0.1 seconds to about 10 seconds, or about 0.1 seconds to about 1 second, or from about 1 millisecond to about 200 milliseconds, or from about 1 millisecond to about 0.5 seconds.

The frequency of the ultrasound energy can be in a range from about 0.1 MHz to about 100 MHz, or from about 0.1 MHz to about 50 MHz, or from about 1 MHz to about 50 MHz or about 0.1 MHz to about 30 MHz, or from about 10 MHz to about 30 MHz, or from about 0.1 MHz to about 20 MHz, or from about 1 MHz to about 20 MHz, or from about 20 MHz to about 30 MHz.

The frequency of the ultrasound energy can be in a range from about 1 MHz to about 12 MHz, or from about 5 MHz to about 15 MHz, or from about 2 MHz to about 12 MHz or from about 3 MHz to about 7 MHz.

In some embodiments, the ultrasound energy can be transmitted to depths at or below a skin surface in a range from about 0 mm to about 150 mm, or from about 0 mm to about 100 mm, or from about 0 mm to about 50 mm, or from about 0 mm to about 30 mm, or from about 0 mm to about 20 mm, or from about 0 mm to about 10 mm, or from about 0 mm to about 5 mm. In some embodiments, the ultrasound energy can be transmitted to depths below a skin surface in a range from about 5 mm to about 150 mm, or from about 5 mm to about 100 mm, or from about 5 mm to about 50 mm, or from about 5 mm to about 30 mm, or from about 5 mm to about 20 mm, or from about 5 mm to about 10 mm. In some embodiments, the ultrasound energy can be transmitted to depths below a skin surface in a range from about 10 mm to about 150 mm, or from about 10 mm to about 100 mm, or from about 10 mm to about 50 mm, or from about 10 mm to about 30 mm, or from about 10 mm to about 20 mm, or from about 0 mm to about 10 mm.

In some embodiments, the ultrasound energy can be transmitted to depths at or below a skin surface in the range from about 20 mm to about 150 mm, or from about 20 mm to about 100 mm, or from about 20 mm to about 50 mm, or from about 20 mm to about 30 mm. In some embodiments, the ultrasound energy can be transmitted to depths at or below a skin surface in a range from about 30 mm to about 150 mm, or from about 30 mm to about 100 mm, or from about 30 mm to about 50 mm. In some embodiments, the ultrasound energy can be transmitted to depths at or below a skin surface in a range from about 50 mm to about 150 mm, or from about 50 mm to about 100 mm. In some embodiments, the ultrasound energy can be transmitted to depths at or below a skin surface in a range from about 20 mm to about 60 mm, or from about 40 mm to about 80 mm, or from about 10 mm to about 40 mm, or from about 5 mm to about 40 mm, or from about 0 mm to about 40 mm, or from about 10 mm to about 30 mm, or from about 5 mm to about 30 mm, or from about 0 mm to about 30 mm.

In various embodiments, a temperature of tissue receiving the ultrasound energy can be in a range from 30° C. to about 100° C., or from 43° C. to about 60° C., or from 50° C. to about 70° C., or from 30° C. to about 50° C., or from 43° C. to about 100° C., or from 33° C. to about 100° C., or from 30° C. to about 65° C., or from 33° C. to about 70° C., as well as variations thereof.

Also, depending at least in part upon a specific biological effect and the tissue layers that are targeted, temperature of tissue receiving the ultrasound energy within ROI 215 may change in a range from approximately 10° C. to about 15° C. In various embodiments, a temperature of tissue receiving the ultrasound energy is raised to a temperature in a range from about 40° C. to about 55° C., or from about 43° C. to about 48° C., or below a threshold of ablation of the tissue.

Figure 2:
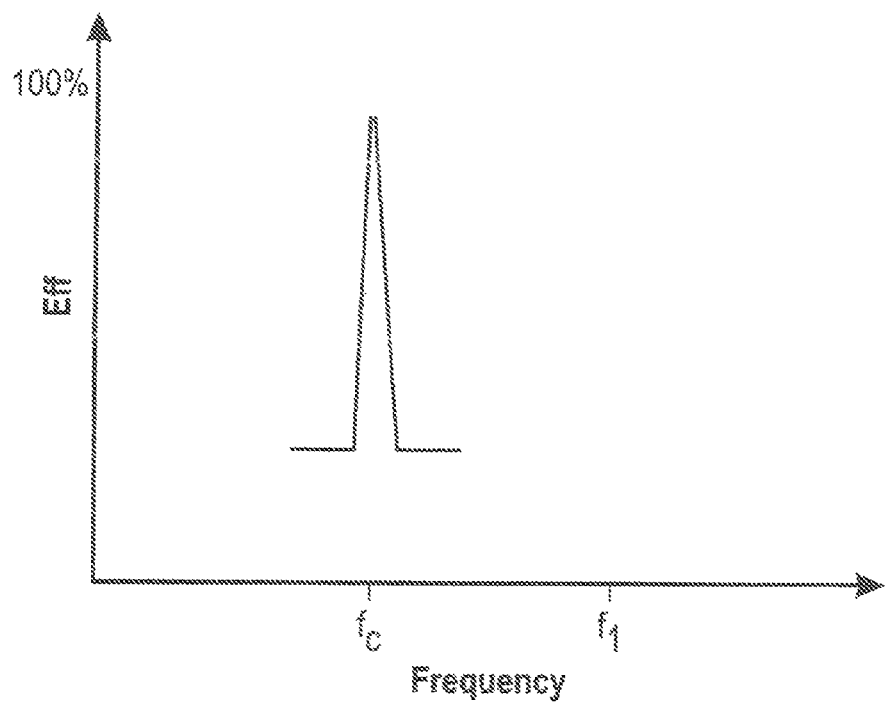
FIG. 2 is a graph illustrating ultrasound efficiency at a frequency, in accordance with various non-limiting embodiments.

Moving to FIG. 2, a graph illustrates efficiency of an ultrasound transducer at specific frequency $f_c$, in accordance with various embodiments. Efficiency of a transducer is defined as the ratio of the power output in the desired form to the total power input. Mathematically, if $P_{in}$ represents the total power input and $P_{out}$ represents the power output in the desired form, then the efficiency E, as a ratio between 0 and 1, is given by:

$$E = P_{out}/P_{in} \quad \text{Equation 1}$$

If E% represents the efficiency as a percentage, then:

$$E\% = 100 P_{out}/P_{in} \quad \text{Equation 2}$$

In general, a transducer is not 100% efficient and power is typically lost during the operation of the transducer in the form of heat. However, for a high-Q transducer, efficiency can approach 100% and heat generated by the transducer is minimized. A transducer is most efficient at specific frequency $f_c$, as illustrated in FIG. 2. The transducer has the maximum power output at frequency $f_c$.

Figure 3:
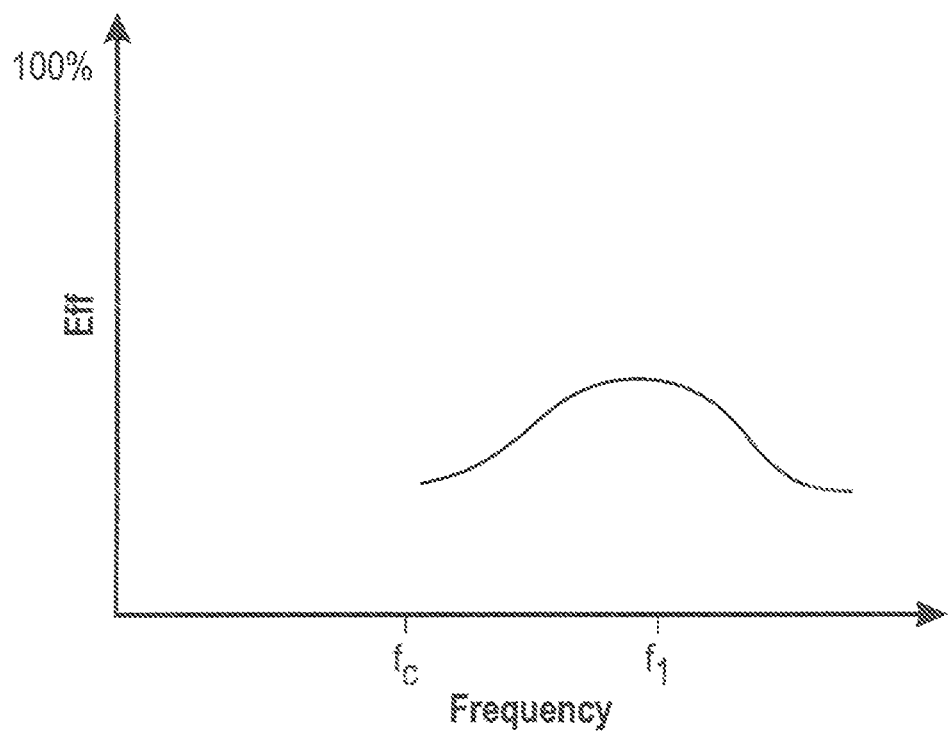
FIG. 3 is a graph illustrating ultrasound efficiency a frequency, in accordance with various non-limiting embodiments.

When a transducer operates, the transducer heats up over time and the temperature of the transducer changes. As the temperature of the transducer changes, the resonant frequency will shift towards frequency $f_t$, as illustrated in FIG. 3. This frequency shift decreases the efficiency of the transducer and, the power output from the transducer is significantly lower in the example of FIG. 3 as compared to the example of FIG. 2.

Transducer efficiency decreases due to changes in temperature of the transducer as a function of time. In addition, a change in temperature of the transducer will cause a frequency shift. The frequency shift changes as a function of increasing temperature of the transducer. A frequency shift decreases efficiency and can cause a system to change total power input to make up for a loss of power applied by the transducer. A frequency shift will change the impedance of the transducer.

In various embodiments, systems and methods, described herein, monitor transducer temperature and report changes in temperature to a controller to modify the frequency generation to the transducer. In various embodiments, systems and methods can monitor transducer temperature and report changes in temperature to a controller to modify the total power input to the transducer. In various embodiments, systems and methods can monitor efficiency and controls transducer temperature to prevent energy transmission from a shift in frequency.

In various embodiments, systems and methods can at least one of monitor transducer temperature and control transducer temperature. In various embodiments, systems and methods can operate the transducer to at or near maximum efficiency of power over a period of time. In various embodiments, systems and methods can operate the transducer to at or near maximum efficiency of power as a temperature of the transducer changes. In various embodiments, systems and methods can modify temperature of the transducer to maintain operation at or near maximum efficiency of power. In various embodiments, systems and methods can prevent a change in impedance of the transducer.

In some embodiments, energy emission, such as, an ultrasound emission, can be directed to targeted tissue to initiate a desired treatment to the targeted tissue. If the power of the energy emission, such as, an ultrasound emission, is too high, the targeted tissue can be permanently damaged, which provide pain to the patient being treated. In addition, if the power of the energy emission, such as, an ultrasound emission, is too high, the desired treatment to the targeted tissue may not be effective. If the power of the energy emission, such as, an ultrasound emission, is too low, the desired treatment to the targeted tissue may not be effective.

If the efficiency of the transducer degrades, the power of energy emission decreases. If the temperature of the transducer changes, the efficiency of the transducer changes and the power of energy emission decreases. For the most effective treatment to targeted tissue, power of energy emission is constant. Various embodiments provide methods and systems to provide constant energy emission from transducer 110 that is directed to targeted tissue.

Figure 4:
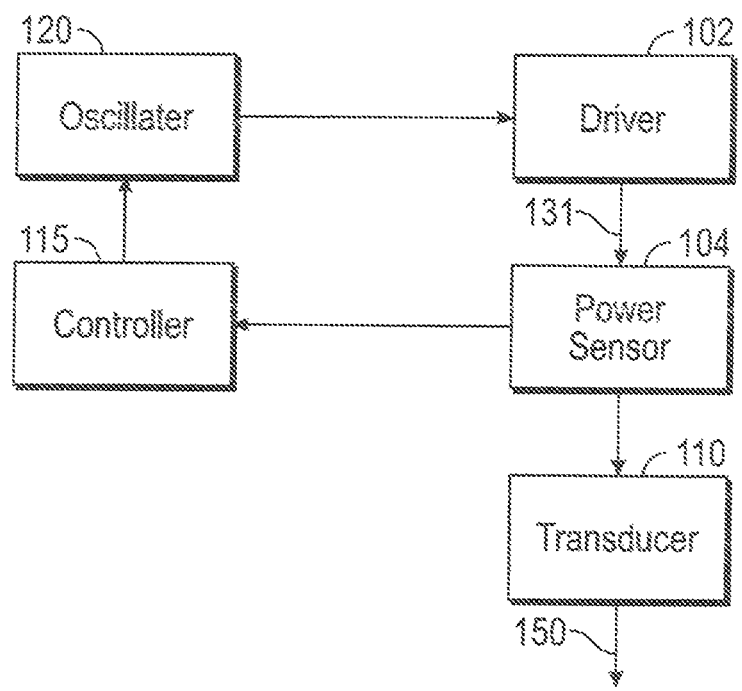
FIG. 4 is a block diagram illustrating a system in accordance with various non-limiting embodiments.

Referring to FIG. 4, system 131 is illustrated, in accordance with some embodiments. System 131 can comprise drivers 102, power sensor 104, transducer 110, controller 115, and oscillator 120. In various embodiments, oscillator 120 generates a frequency which is communicated to drivers 102 to power transducer 110 to produce energy transmission 150 at the frequency. Oscillator 120 can be an oscillator or any frequency generator, now known or later developed. For example, oscillator 120 can be but is not limited to, a function generator, a frequency generator, a waveform generator, a signal generator, pitch generator, a wave generator, or a pulse generator, frequency synthesizer, direct digital synthesizer, or combinations thereof. In some embodiments, oscillator 120 can be combined with or integrated to drivers 102. In some embodiments, oscillator 120 is programmable. In some embodiments, controller 115 can be combined with or integrated to at least one of oscillator 120 and drivers 102. In some embodiments, power sensor 104 can be combined with or integrated to at least one of oscillator 120, controller 115 and drivers 102. In sonic embodiments, power sensor 104 can be combined with or integrated to at least one of oscillator 120, and drivers 102. In some embodiments, power sensor 104 can be combined with or integrated to at least one of controller 115 and drivers 102. In sonic embodiments, power sensor 104 can be combined with or integrated to at least one of oscillator 120, and controller 115. In some embodiments, power sensor 104 can be combined with or integrated to drivers 102. In some embodiments, power sensor 104 can be combined with or integrated to oscillator 120. In some embodiments, power sensor 104 can be combined with or integrated to controller 115.

In some embodiments, power sensor 104 monitors power input from drivers 102 to transducer 110. In some embodiments, power sensor 104 communicates with controller 115, which controls oscillator 120. In some embodiments, controller 115 receives signal from power sensor 104 and controls a frequency generated by oscillator 120 based on the received signal. In some embodiments, power sensor 104 communicates a power level of the power input from drivers 102.

As transducer 110 efficiency of energy transmission 150 degrades, for example as illustrated in FIG. 3, drivers 102 changes the power input to transducer 110. In some embodiments, power sensor 104 detects the change in power input to transducer 110 and communicates with controller 115, which controls oscillator 120 to change in the power level of the power input from supply and/or drivers 102. In some embodiments, oscillator 120 generates a correction to the frequency which is communicated to the drivers 102, which is based on the communication from the power sensor 104. In some embodiments, the correction to the frequency lowers the power level of power input from drivers 102. In some embodiments, energy transmission 150 is corrected to specific frequency $f_c$ as illustrated in FIG. 2. If this correction to specific frequency $f_c$ does not lower the power input from the drivers 102 to transducer 110 below a threshold, power sensor 104 communicates this elevated power level to controller 115, which controls oscillator 120 for another generation of a correction to the frequency. In some embodiments, system 131 comprises a shut off power function, which is initiated if power sensor 104 detects a power level that is above a predetermined threshold. In some embodiments, the shut off power function prevents the damaging or destroying of transducer 110.

In some embodiments, the thickness of the transduction element of transducer 110 may be configured to be uniform. That is, the transduction element may be configured to have a thickness that is generally substantially the same throughout. In another exemplary embodiment, the transduction element may also be configured with a variable thickness, and/or as a multiple damped device. For example, the transduction element of transducer 110 may be configured to have a first thickness selected to provide a specific operating frequency of a lower range, for example from approximately 1 kHz to 3 MHz. The transduction element may also be configured with a second thickness selected to provide a specific operating frequency of a higher range, for example from approximately 3 to 100 MHz or other frequency ranges described herein.

In yet another exemplary embodiment, transducer 110 may be configured as a single broadband transducer excited with two or more frequencies to provide an adequate output for raising the temperature within ROI 215 to the desired level. Transducer 110 may also be configured as two or more individual transducers, wherein each transducer 110 may comprise a transduction element. The thickness of the transduction elements may be configured to provide specific-operating frequencies in a desired treatment range. For example, in some embodiments, transducer 110 may comprise a first transducer 110 configured with a first transduction element having a thickness corresponding to a specific frequency range of approximately 1 MHz to 3 MHz, and a second transducer 110 configured with a second transduction element having a thickness corresponding to a specific frequency of approximately 3 MHz to 100 MHz or frequency ranges described herein.

Moreover, in some embodiments, any variety of mechanical lenses or variable focus lenses, e.g. liquid-filled lenses, may also be used to focus and or defocus the energy field. For example, transducer 110 may also be configured with an electronic focusing array in combination with one or more transduction elements to facilitate changed flexibility in treating ROI 215. Array may be configured in a manner similar to transducer 110. That is, array may be configured as an array of electronic apertures that may be operated by a variety of phases via variable electronic time delays. Accordingly, the electronic apertures of array may be manipulated, driven, used, configured to produce and/or deliver energy in a manner corresponding to the phase variation caused by the electronic time delay. For example, these phase variations may be used to deliver defocused beams, planar beams, and/or focused beams, each of which may be used in combination to achieve different physiological effects in ROT 215.

Transduction elements may be configured to be concave, convex, and/or planar. For example, transduction elements can be configured to be concave in order to provide focused energy for treatment of ROI 215. In another exemplary embodiment, transduction elements may be configured to be substantially flat in order to provide substantially uniform energy to ROI 215. In addition, transduction elements may be configured to be any combination of concave, convex, and/or substantially flat structures. For example, a first transduction element may be configured to be concave, while a second transduction element may be configured to be substantially flat.

Moreover, transduction element can be any distance from the skin surface 204. In that regard, it can be far away from the skin surface 204 disposed within a long transducer 110 or it can be just a few millimeters from skin surface 204. In certain exemplary embodiments, positioning the transduction element closer to skin surface 204 is better for transmitting ultrasound at high frequencies. Moreover, both two and three dimensional arrays of transduction elements can be used in various embodiments.

In some embodiments, transducer 110 may also be configured as an annular array to provide planar, focused and/or defocused acoustical energy. For example, in some embodiments, an annular array may comprise a plurality of rings. Rings may be mechanically and electrically isolated into a set of individual elements, and may create planar, focused, or defocused waves. For example, such waves can be specified on-axis, such as by methods of adjusting corresponding phase delays. An electronic focus may be moved along various depth positions in ROI 215, and may enable variable strength or beam tightness, while an electronic defocus may have varying amounts of defocusing. In some embodiments, a lens and/or convex or concave shaped annular array may also be provided to aid focusing or defocusing such that any time differential delays can be reduced. Movement of annular array in one, two or three-dimensions, or along any path, such as through use of probes, motion mechanisms, any conventional robotic arm mechanisms, and the like may be implemented to scan and/or treat a volume or any corresponding space within ROI 215.

Figure 5:
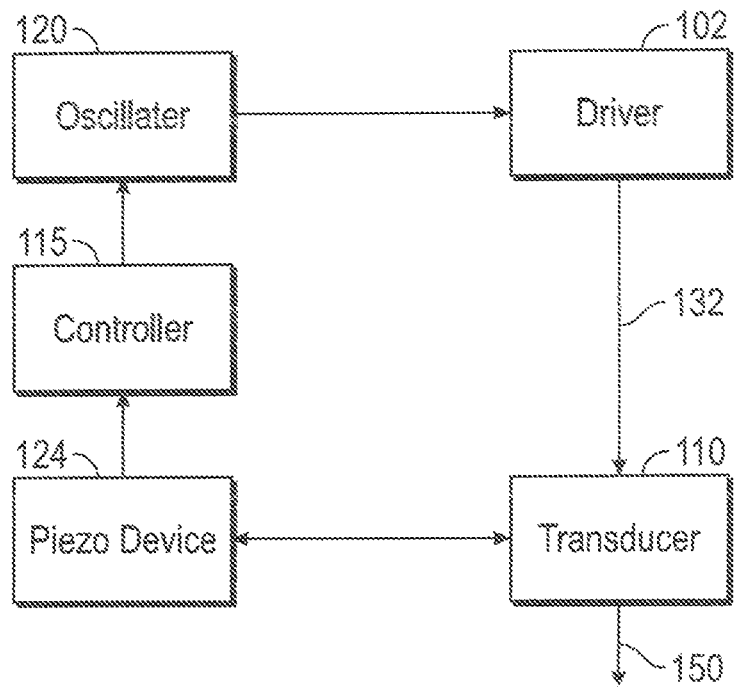
FIG. 5 is a block diagram illustrating a system in accordance with various non-limiting embodiments.

In FIG. 5, system 132 is illustrated, in accordance with some embodiments. System 132 can comprise drivers 102, transducer 110, piezoelectric sensor 124, controller 115, and oscillator 120. In some embodiments, piezoelectric sensor 124 can be combined with or integrated to at least one of oscillator 120 and drivers 102. In some embodiments, piezoelectric sensor 124 can be combined with or integrated into oscillator 120. In some embodiments, piezoelectric sensor 124 can be combined with into integrated to drivers 102. In various embodiments, oscillator 120 generates a frequency which is communicated to drivers 102 to power transducer 110 to produce energy transmission 150 at the frequency. In some embodiments, piezoelectric sensor 124 monitors heat generated by transducer 110. In some embodiments, piezoelectric sensor 124 is coupled to transducer 110. In some embodiments, piezoelectric sensor 124 is integrated to transducer 110. For example, piezoelectric sensor 124 may be a portion of transducer 110, which that is isolated or insulation from the rest of transducer 110, and may comprise identical materials as transducer 110. However, in one aspect of this example, piezoelectric sensor 124 has the opposite temperature coefficient of transducer (same coefficient but opposite sign) and the piezoelectric sensor 124 changes temperature at the same rate as transducer 110, thus compensating for changes in temperature of transducer 110.

Piezoelectric sensor 124 can comprise ceramic, or any other material or combination of material described herein. In some embodiments, piezoelectric sensor 124 is configured with a temperature coefficient that is lower than the temperature coefficient of transducer 110. In some embodiments, piezoelectric sensor 124 is configured with temperature coefficient, which is negative. In various embodiments, piezoelectric sensor 124 generates an electric potential in response to a temperature change, and communicates this electric potential to controller 115, which controls oscillator 120. In some embodiments, piezoelectric sensor 124 communicates with oscillator 120. In some embodiments, controller 115 receives signal from piezoelectric sensor 124 and controls a frequency generated by oscillator 120 based on the received signal. In some embodiments, piezoelectric sensor 124 communicates the heat generated by transducer 110, which can be communicated using temperature.

As transducer 110 efficiency of energy transmission 150 degrades, for example as illustrated in FIG. 3, heat generated by transducer 110 changes. For example, drivers 102 changes the power input to transducer 110, which can change the heat generated by transducer 110. In some embodiments, piezoelectric sensor 124 detects the change in heat generation by transducer 110 and communicates with controller 115, which controls oscillator 120, the change in heat generation. In some embodiments, oscillator 120 generates a correction to the frequency which is communicated to the drivers 102, which is based on the communication from the piezoelectric device 124. In some embodiments, the correction to the frequency lowers the power level of power input from drivers 102, which can lower the amount of heat that is generated by transducer 110. In some embodiments, the correction to the frequency lowers the power level of power input from drivers 102. In some embodiments, energy transmission 150 is corrected to specific frequency $f_c$ as illustrated in FIG. 2. If this correction to specific frequency $f_c$ does not lower the power input from the drivers 102 to transducer 110 below a threshold, piezoelectric sensor 124 communicates this elevated heat generation by transducer 110 to oscillator 124 for another generation of a correction to the frequency. In some embodiments, system 132 comprises a shut off power function, which is initiated if piezoelectric sensor 124 detects a heat generation level or a temperature of transducer 110 is above a predetermined threshold. In some embodiments, the shut off power function prevents the damaging or destroying of transducer 110.

Figure 6:
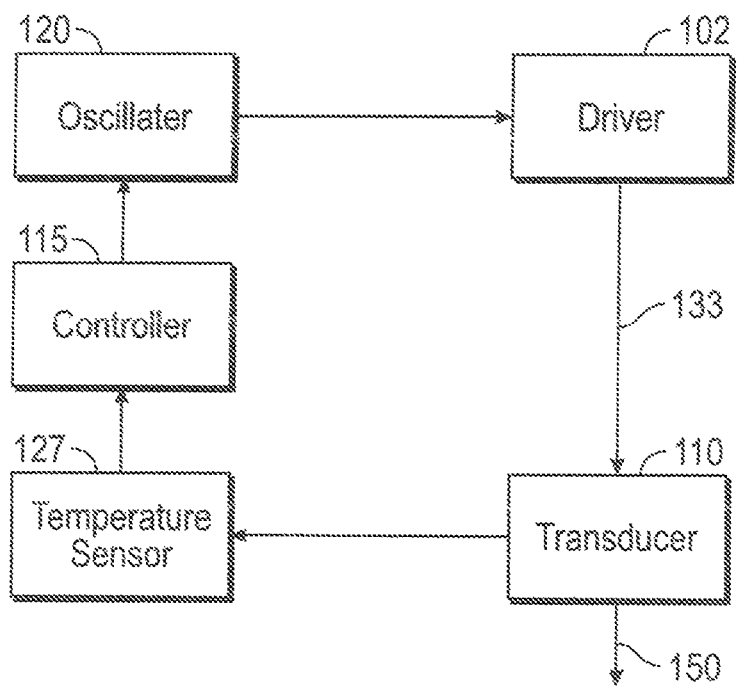
FIG. 6 is a block diagram illustrating a system in accordance with various non-limiting embodiments.

Turning to FIG. 6, system 133 is illustrated, in accordance with some embodiments. System 133 can comprise drivers 102, transducer 110, temperature sensor 127, and oscillator 120. In some embodiments, temperature sensor 127 can be combined with or integrated to at least one of oscillator 120 and drivers 102. In various embodiments, oscillator 120 generates a frequency which is communicated to drivers 102 to power transducer 110 to produce energy transmission 150 at the frequency. In some embodiments, temperature sensor 127 monitors temperature of transducer 110. In some embodiments, temperature sensor 127 coupled to transducer 110. In some embodiments, temperature sensor 127 is integrated to transducer 110. Temperature sensor 127 can be any suitable temperature sensor, now known or later developed. In some embodiments, temperature sensor 127 communicates with controller 115, which communicates with oscillator 120. In some embodiments, temperature sensor 127 communicates with oscillator 120. In some embodiments, controller 115 receives signal from temperature sensor 127 and controls a frequency generated by oscillator 120 based on the received signal. In some embodiments, temperature sensor 127 communicates the temperature of by transducer 110.

As transducer 110 efficiency of energy transmission 150 degrades, for example as illustrated in FIG. 3, heat generated by transducer 110 changes. For example, drivers 102 changes the power input to transducer 110, which can change the heat generated by transducer 110. In some embodiments, temperature sensor 127 detects the change in heat generation by transducer 110 and communicates with controller 115, which controls oscillator 120, the change in heat generation. In some embodiments, oscillator 120 generates a correction to the frequency which is communicated to the drivers 102, which is based on the communication from the piezoelectric device 124. In some embodiments, the correction to the frequency lowers the power level of power input from drivers 102, which can lower the amount of heat that is generated by transducer 110. In some embodiments, the correction to the frequency lowers the power level of power input from drivers 102. In some embodiments, energy transmission 150 is corrected to specific frequency $f_c$ as illustrated in FIG. 2. If this correction to specific frequency $f_c$ does not lower the power input from the drivers 102 to transducer 110 below a threshold, temperature sensor 127 communicates this elevated heat generation by transducer 110 to oscillator 124 for another generation of a correction to the frequency. In some embodiments, system 132 comprises a shut off power function, which is initiated if temperature sensor 127 detects a heat generation level or a temperature of transducer 110 is above a predetermined threshold. In some embodiments, the shut off power function prevents the damaging or destroying of transducer 110.

Figure 7:
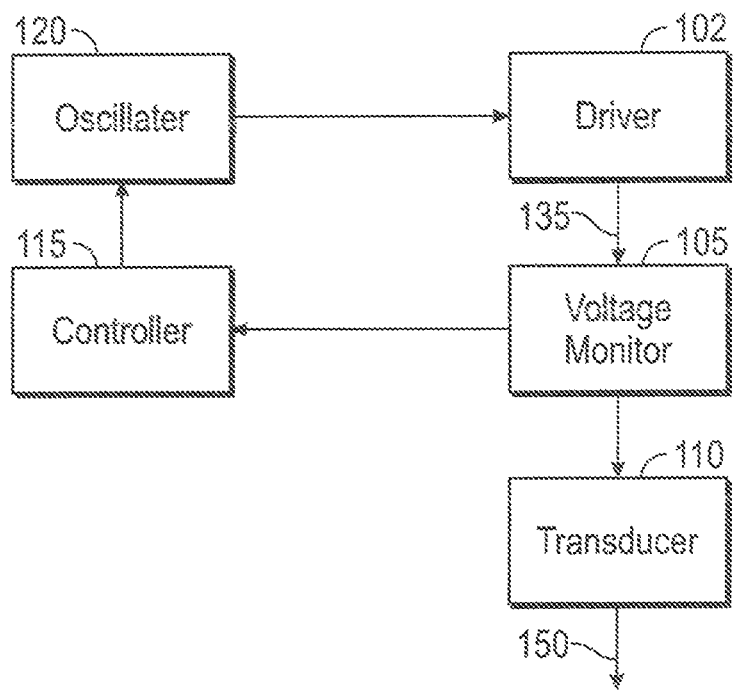
FIG. 7 is a block diagram illustrating a system in accordance with various non-limiting embodiments.

Moving to FIG. 7, system 135 is illustrated, in accordance with some embodiments. System 135 can comprise drivers 102, voltage monitor 105, transducer 110, controller 115, and oscillator 120. In various embodiments, oscillator 120 generates a frequency which is communicated to drivers 102 to power transducer 110 to produce energy transmission 150 at the frequency. Oscillator 120 can be an oscillator or any frequency generator, now known or later developed. For example, oscillator 120 can be but is not limited to, a function generator, a frequency generator, a waveform generator, a signal generator, pitch generator, a wave generator, or a pulse generator, frequency synthesizer, direct digital synthesizer, or combinations thereof. In some embodiments, oscillator 120 can be combined with or integrated to drivers 102. In some embodiments, oscillator 120 is programmable. In some embodiments, controller 115 can be combined with or integrated to at least one of oscillator 120 and drivers 102. In some embodiments, voltage monitor 105 can be combined with or integrated to at least one of oscillator 120, controller 115 and drivers 102. In some embodiments, voltage monitor 105 can be combined with or integrated to at least one of oscillator 120, and drivers 102. In some embodiments, voltage monitor 105 can be combined with or integrated to at least one of controller 115 and drivers 102. In some embodiments, voltage monitor 105 can be combined with or integrated to at least one of oscillator 120, and controller 115. In some embodiments, voltage monitor 105 can be combined with or integrated to drivers 102. In some embodiments, voltage monitor 105 can be combined with or integrated to oscillator 120. In some embodiments, voltage monitor 105 can be combined with or integrated to controller 115. In sonic embodiments, voltage monitor 105 monitors voltage of power from drivers 102 to transducer 110. In some embodiments, voltage monitor 105 communicates with controller 115, which controls oscillator 120. In some embodiments, controller 115 receives signal from voltage monitor 105 and controls a frequency generated by oscillator 120 based on the received signal. In some embodiments, voltage monitor 105 communicates a voltage level of the voltage of power from drivers 102.

As transducer 110 efficiency of energy transmission 150 degrades, for example as illustrated in FIG. 3, drivers 102 changes the voltage of power to transducer 110. In some embodiments, voltage monitor 105 detects the increase in voltage of power to transducer 110 and communicates with controller 115, which controls oscillator 120 to change in the voltage level of the voltage of power from supply and/or drivers 102. In some embodiments, oscillator 120 generates a correction to the frequency which is communicated to the drivers 102, which is based on the communication from the voltage monitor 105. In some embodiments, the correction to the frequency lowers the voltage level of voltage of power from drivers 102. In some embodiments, energy transmission 150 is corrected to specific frequency fc as illustrated in FIG. 2. If this correction to specific frequency fc does not lower the voltage of power from the drivers 102 to transducer 110 below a threshold, voltage monitor 105 communicates this elevated voltage level to controller 115, which controls oscillator 120 for another generation of a correction to the frequency. In some embodiments, system 135 comprises a shut off power function, which is initiated if voltage monitor 105 detects a voltage level that is above a predetermined threshold. In some embodiments, the shut off power function prevents the damaging or destroying of transducer 110.

Figure 8:
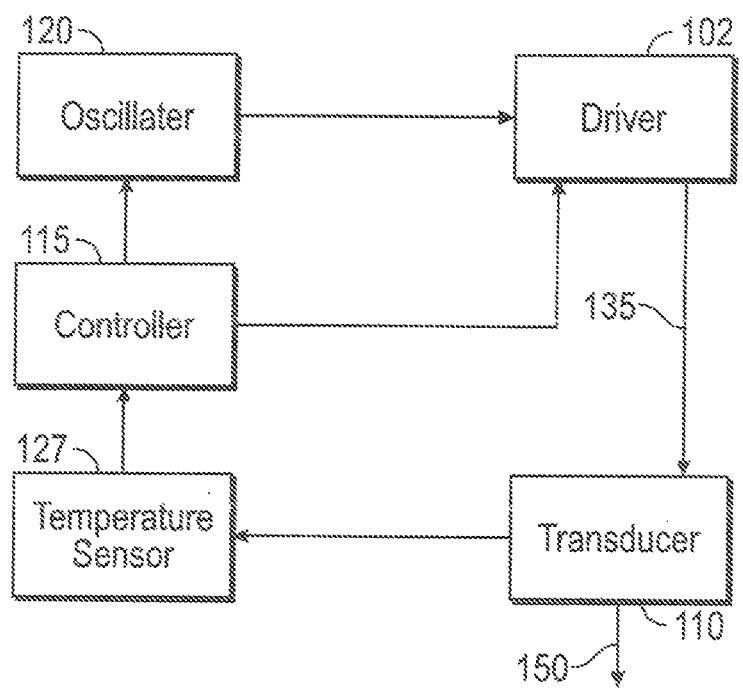
FIG. 8 is a block diagram illustrating a system in accordance with various non-limiting embodiments.

FIG. 8 With reference to FIG. 8, system 135 is illustrated, in accordance with some embodiments. System 135 can comprise drivers 102, transducer 110, temperature sensor 127, and oscillator 120. In some embodiments, temperature sensor 127 can be combined with or integrated to at least one of oscillator 120 and drivers 102. In various embodiments, oscillator 120 generates a frequency which is communicated to drivers 102 to power transducer 110 to produce energy transmission 150 at the frequency. In some embodiments, temperature sensor 127 monitors temperature of transducer 110. In some embodiments, temperature sensor 127 coupled to transducer 110. In some embodiments, temperature sensor 127 is integrated to transducer 110. Temperature sensor 127 can be any suitable temperature sensor, now known or later developed. In some embodiments, temperature sensor 127 communicates with controller 115, which communicates with oscillator 120. In some embodiments, temperature sensor 127 communicates with oscillator 120. In some embodiments, controller 115 receives signal from temperature sensor 127 and controls a frequency generated by oscillator 120 based on the received signal. In some embodiments, temperature sensor 127 communicates the temperature of by transducer 110. As transducer 110 efficiency of energy transmission 150 degrades, for example as illustrated in FIG. 3, drivers 102 changes the power to transducer 110, which change the voltage across the transducer 110. In some embodiments, controller 115 detects the change in voltage across transducer 110 and communicates with controller 115. In some embodiments, oscillator 120 generates a correction to the frequency which is communicated to the drivers 102, which is based on the communication from controller 115. In some embodiments, the correction to the frequency lowers the voltage level of voltage across transducer 110. In some embodiments, energy transmission 150 is corrected to specific frequency fc as illustrated in FIG. 2. If this correction to specific frequency fc does not lower the voltage across transducer 110 below a threshold, controller 115 communicates this elevated voltage level to oscillator 120 for another generation of a correction to the frequency.

As transducer 110 efficiency of energy transmission 150 degrades, for example as illustrated in FIG. 3, heat generated by transducer 110 changes. For example, drivers 102 changes the power input to transducer 110, which can change the heat generated by transducer 110. In some embodiments, temperature sensor 127 detects the change in heat generation by transducer 110 and communicates with controller 115, which controls oscillator 120, the change in heat generation. In some embodiments, oscillator 120 generates a correction to the frequency which is communicated to the drivers 102, which is based on the communication from the piezoelectric device 124. In some embodiments, the correction to the frequency lowers the power level of power input from drivers 102, which can lower the amount of heat that is generated by transducer 110. In some embodiments, the correction to the frequency lowers the power level of power input from drivers 102. In some embodiments, energy transmission 150 is corrected to specific frequency fc as illustrated in FIG. 2. If this correction to specific frequency fc does not lower the power input from the drivers 102 to transducer 110 below a threshold, temperature sensor 127 communicates this elevated heat generation by transducer 110 to oscillator 124 for another generation of a correction to the frequency. In some embodiments, system 132 comprises a shut off power function, which is initiated if temperature sensor 127 detects a heat generation level or a temperature of transducer 110 is above a predetermined threshold. In some embodiments, the shut off power function prevents the damaging or destroying of transducer 110.

Various embodiments provide a method of sensing coupling of an ultrasound source to a target. In some embodiments, the method comprises providing an ultrasound sound source comprising a transducer, an acoustically transparent standoff, an acoustic window at a bottom surface of the standoff, and a frequency sweep function coupled to the transducer. In some embodiments, the method can comprise emitting ultrasound energy from the transducer; receiving reflected energy; frequency sweeping the transducer; determining the feedback from the frequency sweep is above a threshold level; and determining of the source is coupled to the target.

In some embodiments, if the feedback from the frequency is above the threshold level, then the source is not coupled to the target. In some embodiments, if the feedback from the frequency is below the threshold level, then the source is coupled to the target.

In some embodiments, the window is a half wavelength thick. In some embodiments, the method can further comprise providing constant average output power from the source. In some embodiments, the method can further comprise terminating power to the source. In sonic embodiments, the sweep frequency has a period, which is calculated using a path length of the standoff and the speed of sound. In some embodiments, the method can further comprise comprising providing ultrasound energy to a target.

Various embodiments provide a system for determining whether an ultrasound source is coupled to a target. In some embodiments, the system comprises an ultrasound source comprising a transducer; an acoustically transparent standoff coupled to the transducer; a half wavelength acoustic window at a bottom surface of the standoff, and a frequency sweep function coupled to the transducer.

In some embodiments, the half wavelength acoustic window is a reflector when the ultrasound source is not coupled to the target.

In some embodiments, the half wavelength acoustic window is transparent to ultrasound energy when the ultrasound source is coupled to the target. In some embodiments, the system can further comprise a power to transducer termination function in communication with the frequency sweep function.

In some embodiments, the frequency sweep function provides a constant average output power from the ultrasound source when the ultrasound source is coupled to the target. In some embodiments, the system can further comprise a lens coupled to the ultrasound source.

Various embodiments provide a system for providing a constant average output of power from an ultrasound source. In some embodiments, the system comprises an ultrasound transducer coupled to a power supply; a controller in communication with the power supply; a chirp function in communication with and operable to monitor the ultrasound transducer; a feedback loop from the chirp function to the controller. In some embodiments, the controller is operable to change a parameter on the transducer based on the feedback to provide a constant average output of power from the ultrasound transducer.

In some embodiments, the system can further comprise a coupling device in acoustic communication with the ultrasound transducer. In some embodiments, the system can further comprise a half wavelength acoustic window in acoustic communication with the ultrasound transducer.

In some embodiments the coupling device contains a medium configured to be transparent to ultrasound energy. In some embodiments, the system can further comprise a contact sensor operable to determine if the ultrasound transducer is coupled to a target. In some embodiments, the controller is operable to control the power supply to change an amount of power provided to the ultrasound transducer.

In various embodiments, ultrasound probe 205 can comprise a tissue contact sensor. In some embodiments, tissue contact sensor communicates whether ultrasound probe 205 is coupled to the ROI 215. The tissue contact sensor may measure a capacity of a skin surface 204 above the ROI 215 and communicate a difference between the capacitance of the contact to the skin surface 204 and the capacitance of air. In some embodiments, the tissue contact sensor is initiated or turned on by pressing ultrasound probe against skin surface 204.

Figure 9:
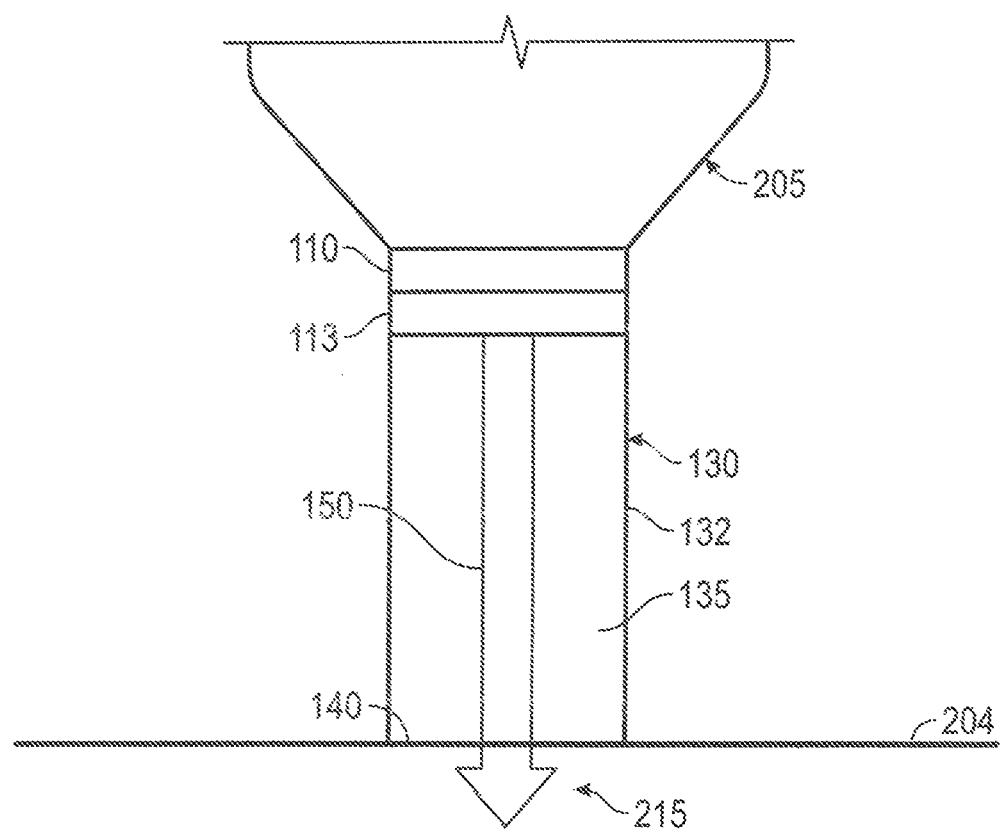
FIG. 9 is a diagram illustrating a transducer system coupled to tissue in accordance to various non-limiting examples.
Figure 10:
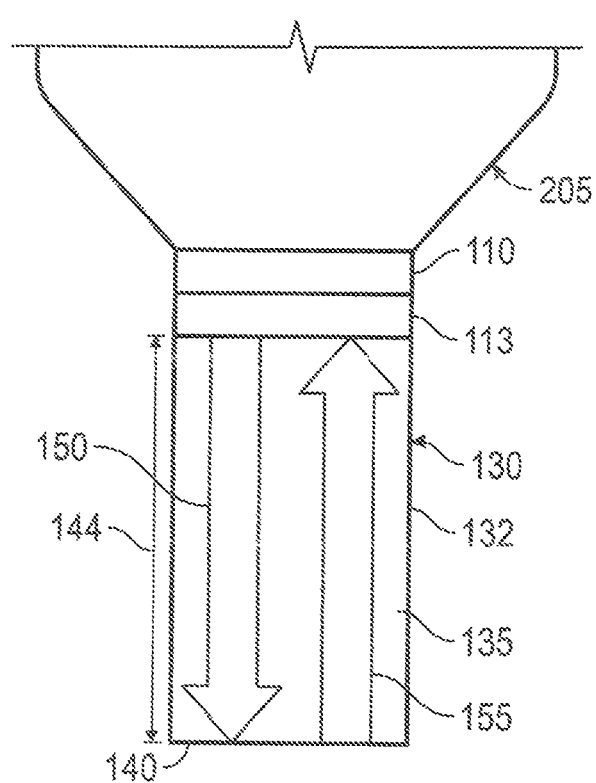
FIG. 10 is a diagram illustrating a transducer system not coupled to tissue in accordance to various non-limiting examples.

In various embodiments, as illustrated in FIGS. 9 and 10, a coupling device having a coupling sensor system is illustrated. Coupling device 130 comprises enclosure 132 which can be filled with coupling medium 135. Coupling device 130 further comprises a window 140 which is essentially transparent to ultrasound energy. In some embodiments, coupling device 130 comprises transducer 110. In some embodiments, coupling device 130 may comprise matching layer and/or lens 113. Coupling device 130 is part of or connects to probe 205. In some embodiments, transducer 110 is separate from the coupling device 130. In some embodiments, transducer 110 and matching layer and/or lens 113 are separate from coupling device 130. Coupling device 130 comprises path length 144, which is the distance from transducer 110 to window 140.

In some embodiments, coupling device 130 is configured to provide ultrasound energy 150 to ROI 215. In some embodiments, coupling device 130 is configured to provide focused ultrasound energy 150 to ROI 215. In some embodiments, coupling device 130 is configured to provide unfocused ultrasound energy 150 to ROI 215. In some embodiments, coupling device 130 is configured to provide defocused ultrasound energy 150 to ROI 215.

In some embodiments, window 140 is a half wavelength ("$\lambda$") thick. In some embodiments, window 140 is a multiple of a half wave length thick, such as, for example, 1.5 wavelength thick. Window 140 can comprise any number of materials that are temperature stable within up to about 150° C. (for example plastics and polymers) or to higher temperatures (for example metals and alloys) and are able to be configured into ultrasound transmissive window having a multiple of a half wave length thick. In some embodiments, window 140 can be configured using a cross linked polystyrene material or a PE imide material.

In some embodiments, enclosure 132 is essentially impermeable to water. Enclosure 132 contains medium 135, which can be water or saline solution or other water based solution, a gel, or a solid. Medium 135 is essentially transparent to acoustic energy. In some embodiments, medium 135 has acoustic impedance very similar to or the same as tissue in the ROI 215. In some embodiments, medium 135 has acoustic impedance very similar to or the same as skin surface.

Figure 11:
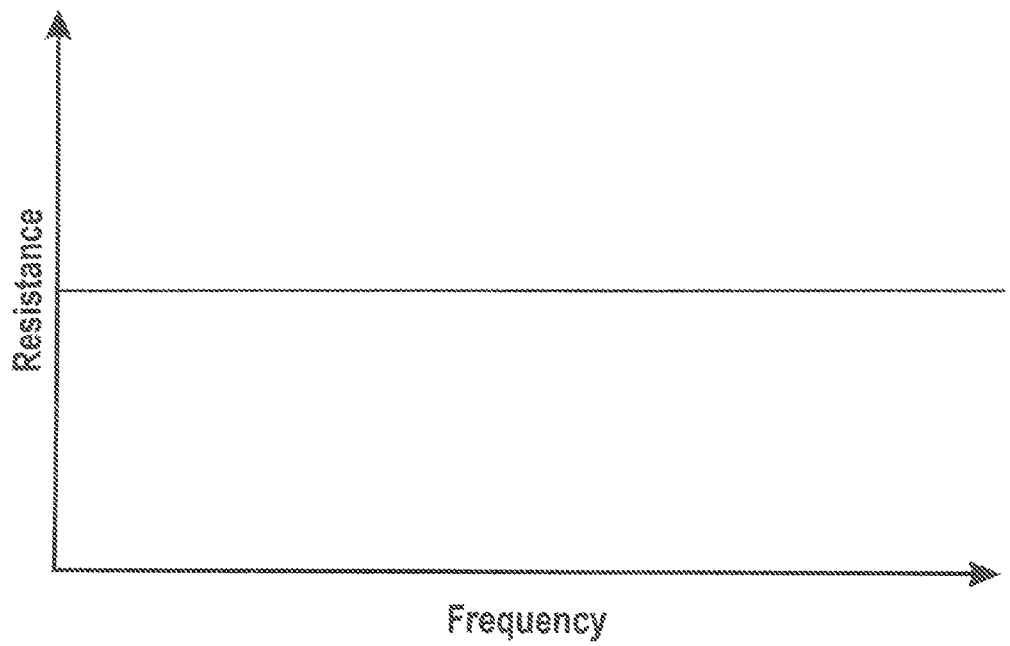
FIG. 11 is a graph illustrating resistance over time for a transducer system coupled to tissue in accordance with various non-limiting embodiments.
Figure 12:
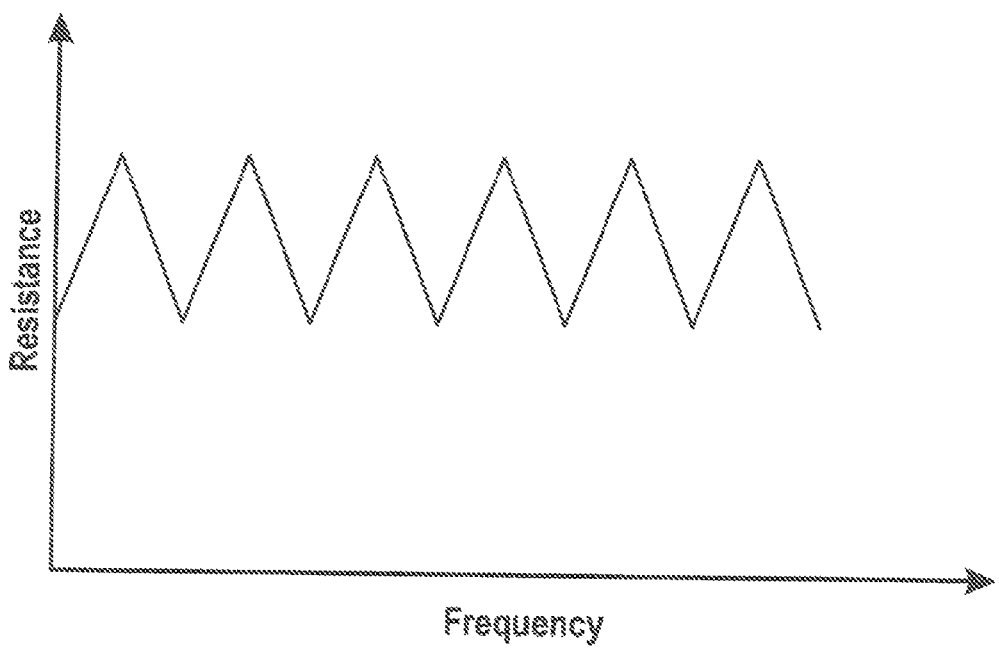
FIG. 12 is a graph illustrating resistance over time for a transducer system not coupled to tissue in accordance with various non-limiting embodiments.

In some embodiments, an output from the frequency sweep can be monitored as illustrated in FIGS. 11 and 12. The units for axis of the graphs in FIGS. 11 and 12 are resistance in the y axis and frequency in the x axis. FIG. 11 illustrates the feedback from a frequency sweep when coupling device 130 is coupled to ROI 215 as illustrated in FIG. 9. FIG. 12 illustrates the feedback from a frequency sweep when coupling device 130 is uncoupled (or coupled to air) as illustrated in FIG. 10. This difference in feedback from the frequency sweep can be a contact sensor. If the frequency sweep reports feedback is similar to FIG. 11, probe 205 continues to function providing ultrasound energy 150 to ROI 215. If the frequency sweep reports feedback is similar to FIG. 12, probe 205 is shut down as a safety mechanism and/or to protect the transducer from being damaged or destroyed.

In some embodiments, a DDS synthesizer and be coupler to transducer 110 and configured to frequency sweep transducer 110. In some embodiments, frequency sweep can monitor the constant average output power of transducer 110. In some embodiments, frequency sweep can be a step function of a set of different frequencies. In some embodiments, the frequency sweep is a chirp function. In some embodiments, the step function of a set of different frequencies can comprise a plurality of different frequencies. In some embodiments, the period of each sweep is 50 kHz. This sweep period is calculated using path length 144 equal to 15 mm and a time of flight of 20 microseconds. In some embodiments, the period of each sweep is 23 kHz. This sweep period is calculated using path length 144 equal to 32.6 mm and a time of flight of 43.5 microseconds. Using path length 144 and the time of flight of the ultrasound energy 150, an appropriate sweep period can be calculated for most configurations of coupling device 130.

In some embodiments, an output from the frequency sweep can be monitored as illustrated in FIGS. 11 and 12. The units for axis of the graphs in FIGS. 11 and 12 are resistance in the y axis and frequency in the x axis. FIG. 11 illustrates the feedback from a frequency sweep when coupling device 130 is coupled to ROI 215 as illustrated in FIG. 9. FIG. 11 illustrates the feedback from a frequency sweep when coupling device 130 is uncoupled (or coupled to air) as illustrated in FIG. 10. This difference in feedback from the frequency sweep can be a contact sensor. If the frequency sweep reports feedback is similar to FIG. 11, probe 205 continues to function providing ultrasound energy 150 to ROI 215. If the frequency sweep reports feedback is similar to FIG. 12, probe 205 is shut down as a safety mechanism and/or to protect the transducer from being damaged or destroyed.

In some embodiments, frequency sweep can monitor and adjust output power to achieve a constant average output power, even with variations in the medium 135 temperature and/or transducer 110 temperature. In various embodiments, contact sensor system can be combined with one or more different sensing techniques. For example, contact sensor can be combined with a hall detector. For example, contact sensor can be combined with an optical detector. For example, contact sensor can be combined with a conductive detector. For example, contact sensor can be combined with a piezo electric detector. For example, contact sensor can be combined with a mechanical detector. For example, contact sensor can be combined with a magnetic detector. In various embodiments, contact sensor system can be combined with at least one of a hall detector, optical detector, an acoustic impedance detector, a conductive detector, a piezo electric detector, a mechanical detector, a magnetic detector, an acoustic impedance detector, and combinations thereof.

In some embodiments, coupling device 130 can comprise a temperature sensor. In some embodiments, coupling device 130 can comprise two temperature sensors. For example, one of the temperature sensors can be in contact with medium 135 and the second temperature sensor can be in contact with transducer 110. In some embodiments, if the temperature as reported by a temperature is above 43° C., probes 205 stop emission of ultrasound energy 150.

The following patents and patent applications are incorporated by reference: US Patent Application Publication No. 20050256406, entitled "Method and System for Controlled Scanning, Imaging, and/or Therapy" published Nov. 17, 2005; US Patent Application Publication No. 20060058664, entitled "System and Method for Variable Depth Ultrasound Treatment" published Mar. 16, 2006; US Patent Application Publication No. 20060084891, entitled "Method and System for Ultra-High Frequency Ultrasound Treatment" published Apr. 20, 2006; U.S. Pat. No. 7,530,958, entitled "Method and System for Combined Ultrasound Treatment" issued May 12, 2009; US Patent Application Publication No. 2008071255, entitled "Method and System for Treating Muscle, Tendon, Ligament, and Cartilage Tissue" published Mar. 20, 2008; U.S. Pat. No. 6,623,430, entitled "Method and Apparatus for Safely Delivering Medicants to a Region of Tissue Using Imaging, Therapy, and Temperature Monitoring Ultrasonic System," issued Sep. 23, 2003; U.S. Pat. No. 7,571,336, entitled "Method and System for Enhancing Safety with Medical Peripheral Device by Monitoring if Host Computer is AC Powered" issued Aug. 4, 2009; US Patent Application Publication No. 20080281255, entitled "Methods and Systems for Modulating Medicants Using Acoustic Energy" published Nov. 13, 2008; US Patent Application Publication No. 20060116671, entitled "Method and System for Controlled Thermal Injury of Human Superficial Tissue," published Jun. 1, 2006; US Patent Application Publication No. 20060111744, entitled "Method and System for Treatment of Sweat Glands," published May 25, 2006; US Patent Application Publication No. 20080294073, entitled "Method and System for Non-Ablative Acne Treatment and Prevention," published Oct. 8, 2009; U.S. Pat. No. 8,133,180, entitled "Method and System for Treating Cellulite," issued Mar. 13, 2012; U.S. Pat. No. 8,066,641, entitled "Method and System for Photoaged Tissue," issued Nov. 29, 2011; U.S. Pat. No. 7,491,171, entitled "Method and System for Treating Acne and Sebaceous Glands," issued Feb. 17, 2009; U.S. Pat. No. 7,615,016, entitled "Method and System for Treating Stretch Marks," issued Nov. 10, 2009; and U.S. Pat. No. 7,530,356, entitled "Method and System for Noninvasive Mastopexy," issued May 12, 2009.

It is believed that the disclosure set forth above encompasses at least one distinct invention with independent utility. While the invention has been disclosed herein, the specific embodiments thereof as disclosed and illustrated herein are not to be considered in a limiting sense as numerous variations are possible. The subject matter of the inventions includes all novel and non-obvious combinations and sub combinations of the various elements, features, functions and/or properties disclosed herein.

Various embodiments and the examples described herein are not intended to be limiting in describing the full scope of systems and methods of this invention. Equivalent changes, modifications and variations of various embodiments, materials, systems, and methods may be made within the scope of the present invention, with substantially similar results.

The invention claimed is:

1. A method of sensing coupling of an ultrasound source to a target, the ultrasound source comprising a transducer, an acoustically transparent standoff, an acoustic window at a bottom surface of the standoff, and a controller coupled to the transducer, the controller configured to execute a frequency sweep over time function, the method comprising:
   emitting an ultrasound energy from the transducer by frequency sweeping over time the transducer using the frequency sweep over time function;
   in response to the emitted ultrasound energy, receiving a reflected energy from the acoustic window;
   determining, using the reflected energy, a feedback from the frequency sweep;
   comparing the feedback with a threshold level; and
   determining, based on the comparison, if the ultrasound source is coupled with the target.

2. The method according to claim 1, wherein if the feedback from the frequency sweep is above the threshold level, then the ultrasound source is not coupled to the target.

3. The method according to claim 2, terminating or reducing power to the ultrasound source.

4. The method according to claim 1, wherein if the feedback from the frequency sweep is below the threshold level, then the ultrasound source is coupled to the target.

5. The method according to claim 4, further comprising providing constant average output power from the ultrasound source.

6. The method according to claim 4, the method further comprising transmitting a second ultrasound energy from the ultrasound source to the target.

7. The method according to claim 1, wherein the acoustic window has a thickness that is a half wavelength of the ultrasound energy or a multiple thereof.

8. The method according to claim 1, the standoff comprising a path length defined as the distance that the ultrasound energy travels through the standoff, wherein the frequency sweep has a frequency span, which is calculated using the path length of the standoff and a speed of sound within the standoff.

9. A system for determining whether an ultrasound source is coupled to a target, the system comprising:
   an ultrasound source comprising a transducer;
   an acoustically transparent standoff coupled to the transducer;
   a half wavelength acoustic window or multiple thereof at a bottom surface of the standoff; and
   a controller coupled to the transducer,
   wherein the controller is configured to cause the transducer to emit ultrasound energy by frequency sweeping over time the transducer using a frequency sweep over time function;
   wherein in response to the emitted ultrasound energy, the transducer is further configured to receive a reflected energy from the half wavelength acoustic window;
   wherein the controller is further configured to determine, using the reflected energy, a feedback from the frequency sweep, compare the feedback with a threshold level, and determine, based on the comparison, if the ultrasound source is coupled with the target.

10. The system according to claim 9, wherein the half wavelength acoustic window is a reflector when the ultrasound source is not coupled to the target.

11. The system according to claim 9, wherein the half wavelength acoustic window is transparent to ultrasound energy when the ultrasound source is coupled to the target.

12. The system according to claim 9, the controller further configured to execute a power to transducer termination function in communication with the frequency sweep over time function.

13. The system according to claim 9 wherein the controller provides a constant average output power from the ultrasound source when the ultrasound source is coupled to the target.

14. The system according to claim 9, further comprising a lens coupled to the ultrasound source.

* * * * *

UNITED STATES PATENT AND TRADEMARK OFFICE
CERTIFICATE OF CORRECTION

| | | |
|---|---|---|
| PATENT NO. | : 9,504,446 B2 | Page 1 of 1 |
| APPLICATION NO. | : 13/547023 | |
| DATED | : November 29, 2016 | |
| INVENTOR(S) | : Paul Jaeger et al. | |

It is certified that error appears in the above-identified patent and that said Letters Patent is hereby corrected as shown below:

In the Specification

Column 10, Line 44 - "ROT" should be -- ROI --

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*